United States Patent [19]

Doherty et al.

[11] 4,440,779

[45] Apr. 3, 1984

[54] TRICYCLIC DERIVATIVES OF SUBSTITUTED PYRROLE ACIDS AS ANALGESIC AND ANTI-INFLAMMATORY AGENTS

[75] Inventors: James B. Doherty, New Milford; Conrad P. Dorn, Plainfield; Bruce E. Witzel, Westfield; Debra L. Allison, Scotch Plains; Tsung-Ying Shen, Westfield, all of N.J.

[73] Assignee: Merck & Co., Inc., Rahway, N.J.

[21] Appl. No.: 385,232

[22] Filed: Jun. 4, 1982

Related U.S. Application Data

[63] Continuation-in-part of Ser. No. 279,140, Jun. 30, 1981, abandoned.

[51] Int. Cl.$^3$ .................... A61K 31/55; C07D 209/94; C07D 491/044
[52] U.S. Cl. ............................. 424/274; 260/239.3 T; 548/427; 548/430; 548/431; 548/450
[58] Field of Search ................. 260/239.3 T; 424/274; 548/427, 431, 430, 450

[56] References Cited

U.S. PATENT DOCUMENTS

3,952,012 4/1976 Carson ................................. 548/450
4,119,639 10/1978 Carson ................................. 548/450

FOREIGN PATENT DOCUMENTS

24807 3/1981 European Pat. Off. ............ 548/450

OTHER PUBLICATIONS

Ackrell et al., *J. Heterocyclic Chem.*, 17, 1081 (1980).

*Primary Examiner*—Robert T. Bond
*Attorney, Agent, or Firm*—Theresa Y. Cheng; Mario A. Monaco

[57] ABSTRACT

Tricyclic derivatives of substituted pyrrole acids, e.g., substituted 4,10-dihydro-10-oxo-1H-[1]benzoxepino[4,3-b]pyrrole-2-acetic acids or the 5-thia analogs thereof have been prepared via hydrolysis of a precursor or decarboxylation of a precursor-diacid. These tricyclic compounds are found to have high analgesic and anti-inflammatory activities but low ulcerogenic side effects.

14 Claims, No Drawings

TRICYCLIC DERIVATIVES OF SUBSTITUTED PYRROLE ACIDS AS ANALGESIC AND ANTI-INFLAMMATORY AGENTS

This application is a continuation-in-part of application Ser. No. 06/279,140, filed June 30, 1981, now abandoned.

BACKGROUND OF THE INVENTION

The present invention relates to tricyclic analgesic and anti-inflammatory agents of the structural formula (I).

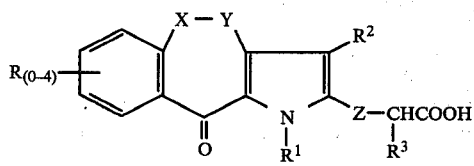

(I)

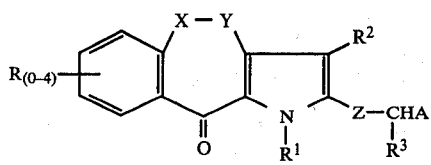

(Ia)

or a pharmaceutically acceptable salt, ester or amide thereof. In addition, the present invention also includes those derivatives which are bioequivalents of compound (I). For example, compounds of formula (Ia) wherein A is —CHO; —CH$_2$OH; or —CN. These novel nonsteroidal-anti-inflammatory agents (NSAIA) also exhibit the actions of analgesia and antipyresis. In other words, they are useful for the treatment of fever, pain and inflammatory conditions, associated with arthritis, spondylitis, gout, dismennohrea, upper respiratory disorders and peridontal diseases.

Accordingly the objectives of the present invention are (1) to provide novel nonsteroidal anti-inflammatory and analgesic agents with high potency but lower ulcerogenic side effects; (2) to develop processes for the preparation of the novel tricyclic compounds; (3) to provide methods of application of the novel tricyclic compounds in the treatment of inflammatory diseases and/or the relief of pain and fever; and (4) to provide pharmaceutical compositions and formulations for the administration of these novel tricyclic compounds.

DETAILED DESCRIPTION OF THE INVENTION

This invention relates to new, nonsteroidal anti-inflammatory agents of the structural formula (I)

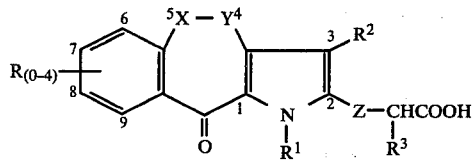

(I)

or a pharmaceutically acceptable salt, ester or amide thereof; or alternatively a bioequivalent thereof where the COOH group of formula (I) is replaced with —CHO, —CH$_2$OH, or —CN, wherein there are 0–4 R groups and R is (a) hydrogen;
(b) lower alkyl especially C$_{1-6}$ alkyl, e.g., methyl, ethyl, isopropyl, t-butyl, pentyl and cyclohexyl;
(c) halo-loweralkyl wherein also is fluoro, chloro, bromo or iodo, and loweralkyl as defined in (b);
(d) hydroxy or lower alkoxy especially C$_{1-6}$ alkoxy such as methoxy, ethoxy, allyloxy, butoxy, cyclopentyloxy, hexyloxy or when there are two sets of R groups, they join and form 7,8-methylenedioxy, 6,7-ethylenedioxy or 7,8-propylenedioxy;
(e) halo such as fluoro, chloro, or bromo;
(f) lower alkylthio especially C$_{1-3}$ alkylthio, e.g., methylthio, ethylthio, propylthio;
(g) lower alkylsulfinyl especially C$_{1-3}$ alkylsulfinyl, e.g., methylsulfinyl, ethylsulfinyl, and propylsulfinyl;
(h) lower alkylsulfonyl especially C$_{1-3}$ alkylsulfonyl, e.g., methylsulfonyl, ethylsulfonyl or propylsulfonyl;
(i) lower alkenyl especially C$_{2-6}$ alkenyl such as ethenyl, propenyl, butenyl, pentenyl and hexenyl;
(j) phenyl;
(k) substituted phenyl such as loweralkyl-, loweralkylsulfinyl, loweralkoxy-, loweralkylthio-, loweralkylsulfonyl-, chloro- or fluoro-substituted phenyl;
(l) carboxy;
(m) carbalkoxy;
(n) cyano;
(o) amino or loweralkylamino especially C$_{1-6}$ alkylamino such as methylamino or ethylamino;
(p) di(loweralkyl)amino especially di-C$_{1-6}$alkylamino such as dimethylamino, dipropylamino, dipentylamino;
(q) lower alkanoyl especially C$_{1-6}$ alkanoyl, e.g., acetyl, propanoyl, butanoyl, and hexanoyl; or
(r) benzoyl or substituted benzoyl such as 4-fluorobenzoyl, 2,4-dichlorobenzoyl, 4-methylbenzoyl or 4-methoxybenzoyl;

R$^1$ is
(a) hydrogen;
(b) lower alkyl;
(c) lower alkenyl;
(d) lower alkanoyl;
(e) phenyl or substituted phenyl;
(f) benzoyl or substituted benzoyl; or
(g) benzyl or substituted benzyl, such as 4-methylbenzyl, 2-methoxybenzyl, 2,4-difluorobenzyl, 4-nitrobenzyl or 4-chlorobenzyl;
(h) lower alkoxy;
(i) lower alkylamino;
(j) di(loweralkyl)amino;

where the definition of groups (b)-(j) above is as previously defined; or (k) hydroxy C$_{1-6}$alkyl especially 2-hydroxyethyl, or 2-hydroxypropyl;

Z is
(a) —(CH$_2$)—$_{0-n}$, where n is 0–10;
(b) —CO(CH$_2$)$_{1-n}$—;
(c) —(CH$_2$)$_{1-n}$—CO—; or

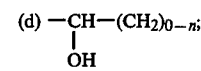

(d)

R$^2$ is
(a) hydrogen;
(b) lower alkyl as previously defined;

(c) lower alkenyl especially $C_{2-6}$ alkenyl such as ethenyl, propenyl, butenyl, pentenyl and hexenyl;
(d) lower alkoxy as previously defined;
(e) —CH$_2$OH;
(f) halo such as chloro, fluoro or bromo; or
(g) phenyl or substituted phenyl as previously defined;

$R^3$ is hydrogen, lower alkyl as previously defined, hydroxy, loweralkoxy, or halo especially fluoro, chloro or bromo; and X-Y is

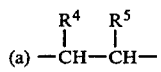

where $R^4$ and $R^5$ independently are hydrogen, loweralkyl, loweralkoxy or halo as previously defined;

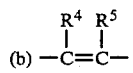

wherein $R^4$ and $R^5$ are as previously defined;
(c) —O—CH$_2$—;
(d) —CH$_2$—O—;
(e) —S—CH$_2$—;
(f) —CH$_2$—S—;
(g) —CO—O—;
(h) —O—CO—;
(i) —CO—NH—; or
(j) —NH—CO—.

The preferred embodiment of this invention comprises compounds of formula (I) or (Ia) wherein:

R is
(a) hydrogen;
(b) $C_{1-4}$ alkyl especially methyl, ethyl or t-butyl;
(c) halo-$C_{1-3}$ alkyl such as trifluoromethyl, trichloromethyl and 1,1-difluoropropyl;
(d) $C_{1-3}$ alkoxy such as methoxy, ethoxy and propoxy;
(e) chloro or fluoro;
(f) $C_{1-3}$ alkylthio such as methylthio, ethylthio;
(g) $C_{1-3}$ alkylsulfinyl such as methylsulfinyl;

$R^1$ is hydrogen or $C_{1-6}$ lower alkyl;

Z is
(a) —(CH$_2$)$_{0-5}$—;
(b) —CO(CH$_2$)$_{1-5}$—;
(c) —(CH$_2$)$_{1-5}$—CO—; or (d) —CH—(CH$_2$)$_{0-5}$;
       |
       OH $R^2$ is
(a) hydrogen;
(b) $C_{1-3}$ alkyl as previously defined;
(c) $C_{1-3}$ alkoxy such as methoxy and ethoxy;

$R^3$ is hydrogen, $C_{1-4}$ alkyl especially methyl or ethyl, $C_{1-4}$ alkoxy, chloro or fluoro; and X-Y is
(a) —CH$_2$—O—;
(b) —O—CH$_2$—;
(c) —CH$_2$—S—; or
(d) —S—CH$_2$.

The most preferred embodiment of this invention comprises compounds of formula (I) or (Ia) wherein R is
(a) $C_{1-3}$ alkyl;
(b) $C_{1-3}$ haloalkyl especially trifluoromethyl;
(c) methoxy or ethoxy;
(d) chloro or fluoro;
(e) methylthio; or
(f) methylsulfinyl;
(g) 7,8-methylenedioxy;

$R^1$ is hydrogen, methyl, ethyl or propyl;
Z is as previously defined;
$R^2$ is
(a) hydrogen; or
(b) $C_{1-3}$ alkyl as previously defined;
$R^3$ is hydrogen, methyl, methoxy or fluoro;
X-Y is
(a) —O—CH$_2$—; or
(b) —S—CH$_2$—.

The subject compounds may be prepared from the hydrolysis of a precursor ester of the structural formula (II).

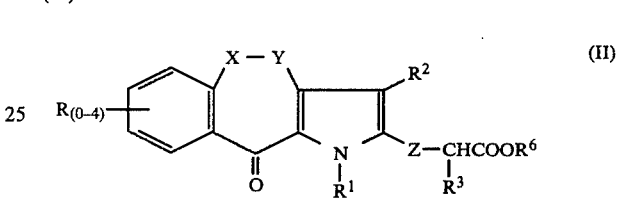

wherein R, $R^1$, $R^2$, $R^3$ and —X—Y— are as previously defined and $R^6$ is loweralkyl as previously defined or an acid-removable protecting group, e.g., t-butyl and benzhydryl, or any other commonly employed protecting group e.g., benzyl or substituted benzyl, trityl, trichloroethyl, β-trimethylsilylethyl and trimethylsilyl.

An ester of formula II is usually treated with an acid (Table I) or a base (Table II) in an appropriate solvent at about 10°–150° C. preferably about 25°–100° C. for about 0.5–48 hours or until the hydrolysis is substantially complete.

The most commonly utilized solvents comprise
(1) water;
(2) $C_{1-5}$ alkanol especially methanol, ethanol, isopropanol and t-butyl alcohol;
(3) lower ketone, e.g. acetone and methylethylketone;
(4) lower ether including diethylether, 1,2-dimethoxyethane, tetrahydrofuran (THF), dioxane and diglyme;
(5) a liquid acid, e.g. acetic acid and trifluoroacetic acid; or
(6) a mixture of at least two of the solvents described in (1) to (5) especially aqueous solutions thereof.

TABLE I

Common Acids Used in Hydrolysis

Hydrochloric acid or hydrobromic acid
Sulfuric acid
Phosphoric acid
$C_{1-3}$ alkanoic acid e.g. acetic acid
Trifluoroacetic acid
Trichloroacetic acid
p-Toluenesulfonic acid

TABLE II

Common Bases Used in Hydrolysis

Sodium hydroxide
Potassium hydroxide

Sodium or potassium carbonate
Sodium or potassium bicarbonate
Calcium hydroxide
Lithium hydroxide
Tetra(loweralkyl)ammonium hydroxide such as tetramethyl or tetraethylammonium hydroxide
Tri-(lower alkyl)amine, e.g., triethylamine
pyridine
collidine Alternatively, the subject compounds (when $R^2$=H) may be prepared from the following precursors:

(1) acidic decarboxylation of a precursor diacid of structural formula (III) or the corresponding di-t-butyl or di-benzhydryl ester thereof.

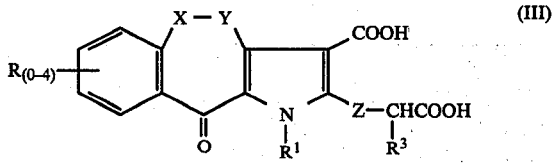

(III)

The decarboxylation is preferably conducted under mild conditions. For example, 7-chloro-3-hydroxycarbonyl-1-methyl-10-oxo-10H-benzocyclohepten [1,2-b]pyrrole-2-acetic acid is treated with refluxing trifluoroacetic acid to afford 7-chloro-1-methyl-10H-10-oxo-benzocycloheptena[1,2-b]pyrrole-2-acetic acid. Other acids may also be used. For example, those listed below in Table III.

TABLE III

Acids Used in the Decarboxylation (1) An acid of the structural formula:

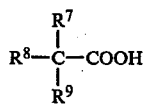

wherein $R^7$ and $R^8$ independently are hydrogen or halo such as iodo, bromo, chloro or fluoro preferably chloro or fluoro; and $R^9$ is H, $C_{1-6}$ alkyl, halo especially chloro or fluoro, or halo-$C_{1-6}$ alkyl such as trifluoromethyl, trichloromethyl, 1,1-difluoroethyl, or 1-chloro-1-fluoropropyl or the like.

(2) Preferred Acids:
Trifluoroacetic acid
Acetic acid
Chloroacetic acid
Chlorodifluoroacetic acid
Dichloroacetic acid
Difluoroacetic acid
Trichloroacetic acid
Pentafluoropropanoic acid The decarboxylation may be conducted in an acid or in an inert solvent containing the acid or neat, i.e., by itself. The solvents which are often used are illustrated below in Table IV.

TABLE IV

Solvents for the Acidic Decarboxylation

Toluene
Benzene
Xylene
Tetrahydrofuran
1,2-Dimethoxyethane
Dioxane

The decarboxylation temperatures may vary with the acids or solvents being used. Usually the temperatures range from about 30° to about 120° C. Under the optimum conditions, i.e., in refluxing trifluoroacetic acid with or without solvent, the temperature ranges from about 35° to about 72° C.

Generally, the decarboxylation is substantially complete after heating at an appropriate temperature for about 1 to about 20 hours or under more favorable conditions, about 0.5 hours.

(2) Conversion from a precursor of formula IIa

The preferred mode of this invention is a class of 7-substituted 10-oxo-1H-[1]benzoxepino[4,3-b]pyrrole-2-acetic acids of formula (IIb), especially 7-methyl or 7-methoxy-4,10-dihydro-1-methyl-10-oxo-1H[1]-benzoxepino[4,3-b]pyrrole-2-acetic acid. These compounds are generally obtainable from
(a) precursor esters of formula (II), page 7;
(b) precursor diacids of formula (III), page 10; or
(c) precursors of formula (IIa) as shown below by procedures well-established in the art.

For example, each of the representative conversions is illustrated in a particular example as shown below in Table V.

TABLE V

Preparation of Substituted
10-oxo-1H-[1]benzoxepino[4,3-b]pyrrole-2-acetic acids
of formula (IIb)

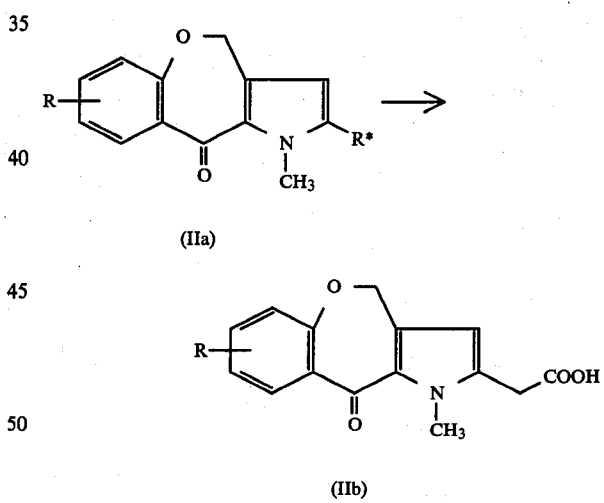

wherein R is as previously defined and is preferably 7-$CH_3$ or 7-$OCH_3$; and R* is as defined below.

| R* | Example No. |
|---|---|
| —$CH_2CONH_2$ | 15 |
| —CH=$CH_2$ | 16 |
| —CHO | 17 |
| —$CH_2CH_2OH$ | 18 |
| —$CH_2CHO$ | 19 |
| —$COCH_3$ | 20 |
| —$CH_2COCl$ | 21 |
| —$CH_2COCOOH$ | 22 |
| —$CH_2COCHO$ | |
| —$CH_2COCOCH_3$ | 23 |
| —$CH_2COCH(OH)CH_3$ | |
| —$CH_2CH(OH)COCH_3$ | |

| R° | Example No. |
|---|---|
| —CH₂(CHOH)₂CH₃ | 24 |
| —CH₂CH(OH)CH(NH₂)CH₃ | |
| —CH₂CH(NH₂)CH(OH)CH₃ | |
| —CH₂CH=CH₂ | 25 |
| —CH₂CX₃ | 26 |
| —COCH₂OCH₃ | 27 |
| —CH₂C(OEt)₃ | 28 |
| —CH₂C(=NH)NH₂ | 29 |
| —CH₂COCR° (R° is loweralkyl) (with two C=O) | 30 |
| —CH(OH)COOH | 31 |
| —CH(NH₂)COOH | 32 |
| —COCH₂COOH | 33 |
| —CH₂CH(OH)COOH | 34 |
| —CH₂CH(NH₂)COOH | 35 |
| —CH₂COCH₂COOR° (R° = loweralkyl) | 36 |
| —CH₂OH | 37 |
| —CH₂X | 38 |
| —H | 39 |
| —CH₃ | 40 |
| —CH₂C≡CH | 41 |
| —CH(COOH)₂ | 42 |
| —CH₂CN | 43 |
| —CH₂C(OEt)=NH | 44 |
| —CH₂COSR° | 45 |
| —CH₂COCH₃ | 46 |
| —CH₂COOt—Bu (with CN substituent) | 47 |
| —CHCOOR° | 48 |
| —CH₂-(oxazine ring) | 49 |
| —CH₂CO₂CH₂—Ph | 50 |
| —COCH₂Br | 51 |
| —C≡CH | 52 |

The starting material of a precursor-ester of formula (II) may be prepared from cyclization of various substituted arylpyrrole-alkanoic acid esters. However, because of the sensitive nature of the pyrrole structure as well as the chemical characteristics of the —X—Y— moiety, no uniform synthetic scheme is applicable to all the precursors of different —X—Y— moieties. Accordingly, as shown below in Table VI, a representative procedure for preparing the starting material of a specific —X—Y— moiety is incorporated in a particular Example, infra.

TABLE VI
Correlation Between —X—Y— and Representative Examples

| X—Y | Example No. |
|---|---|
| —CH₂—O— | 1 (Steps 1–6) |
| —O—CH₂— | 2 (Steps 1–7) |
| —CH₂—CH₂— | 3 (Steps 1–11) |
| —CH=CH— | 4 (derived from —CH₂—CH₂—) |
| —S—CH₂— | 5 (Steps 1–5) |
| —NH—C(=O)— | 6 (Steps 1–6) |

As to the starting material of a precursor-diacid of formula (III), it is usually prepared from the corresponding diesters via hydrolysis. For example, 7-chloro-3-hydroxycarbonyl-1-methyl-10H-10-oxo-benzocyclohepten[1,2-b]pyrrole-2-acetic acid (Example 4, Step 1, infra) is obtained from a precursor of the corresponding monoesters of formula (II). In other words, the representative procedures listed in Table V are also applicable to the preparation of diacids of formula (III).

In addition to the representative examples listed in Table VI, there are several general routes for the preparation of the preferred compounds wherein X-Y is —O—CH₂— or —S—CH₂—. These processes are of special interest and are described below in Schemes I-V:

Scheme I
(illustrated by Example 2)

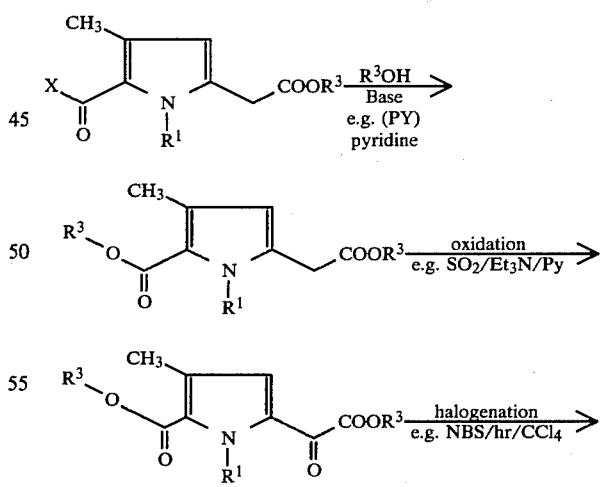

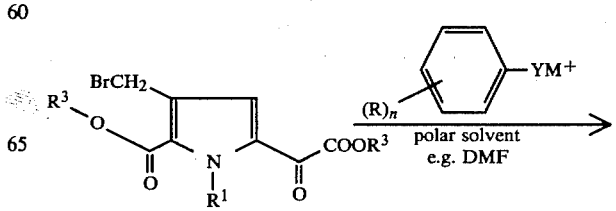

-continued
Scheme I
(illustrated by Example 2)

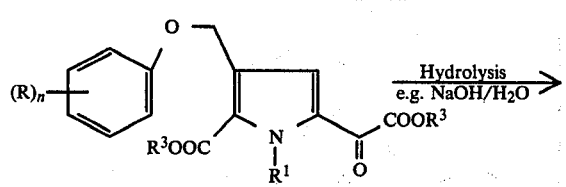 → Hydrolysis e.g. NaOH/H₂O →

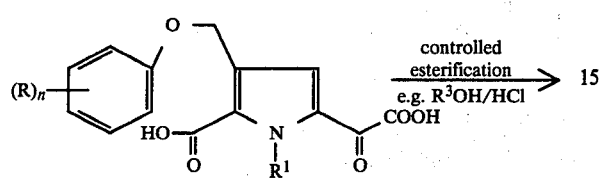 → controlled esterification e.g. R³OH/HCl →

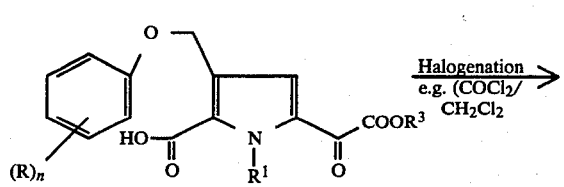 → Halogenation e.g. (COCl)₂/ CH₂Cl₂ →

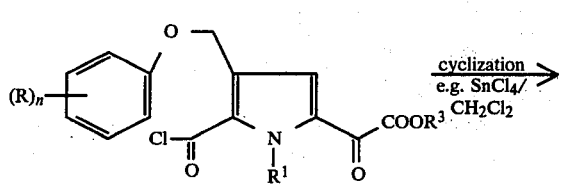 → cyclization e.g. SnCl₄/ CH₂Cl₂ →

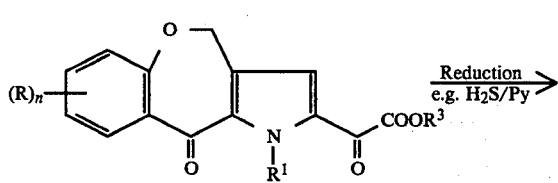 → Reduction e.g. H₂S/Py →

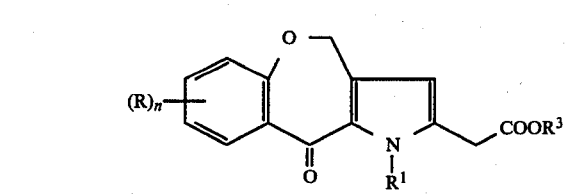

R¹, R and n are as defined previously;
R³ is loweralkyl or other protecting groups for acid function;
X is halo, e.g. Cl, Br.

Scheme II
(Illustrated by Example 11)

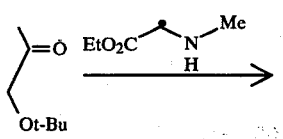

-continued
Scheme II
(Illustrated by Example 11)

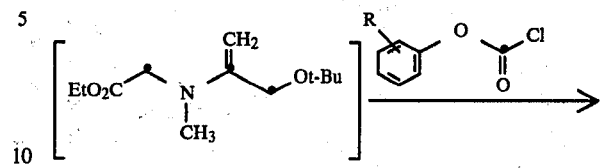 →

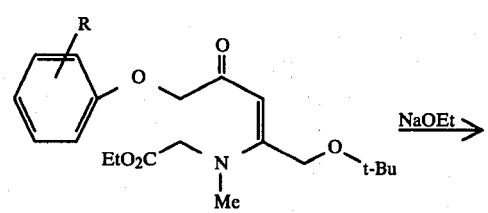 NaOEt →

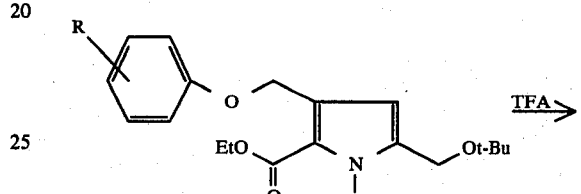 TFA →

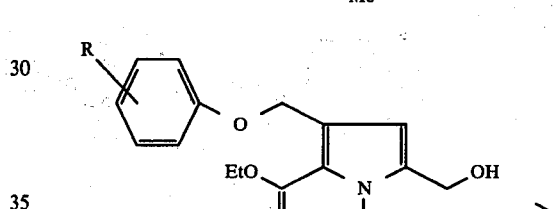 →

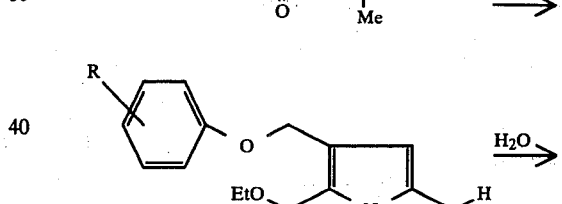 H₂O →

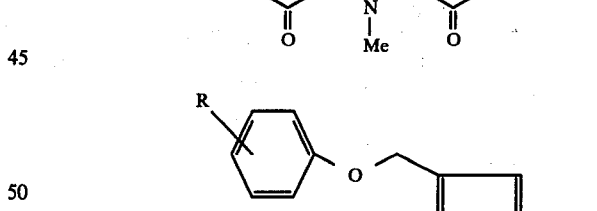 →

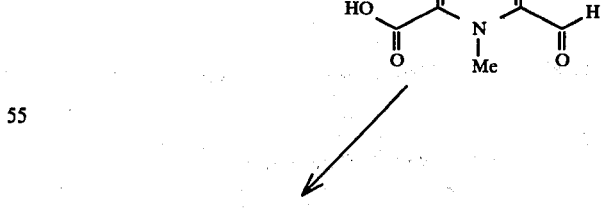

IIa

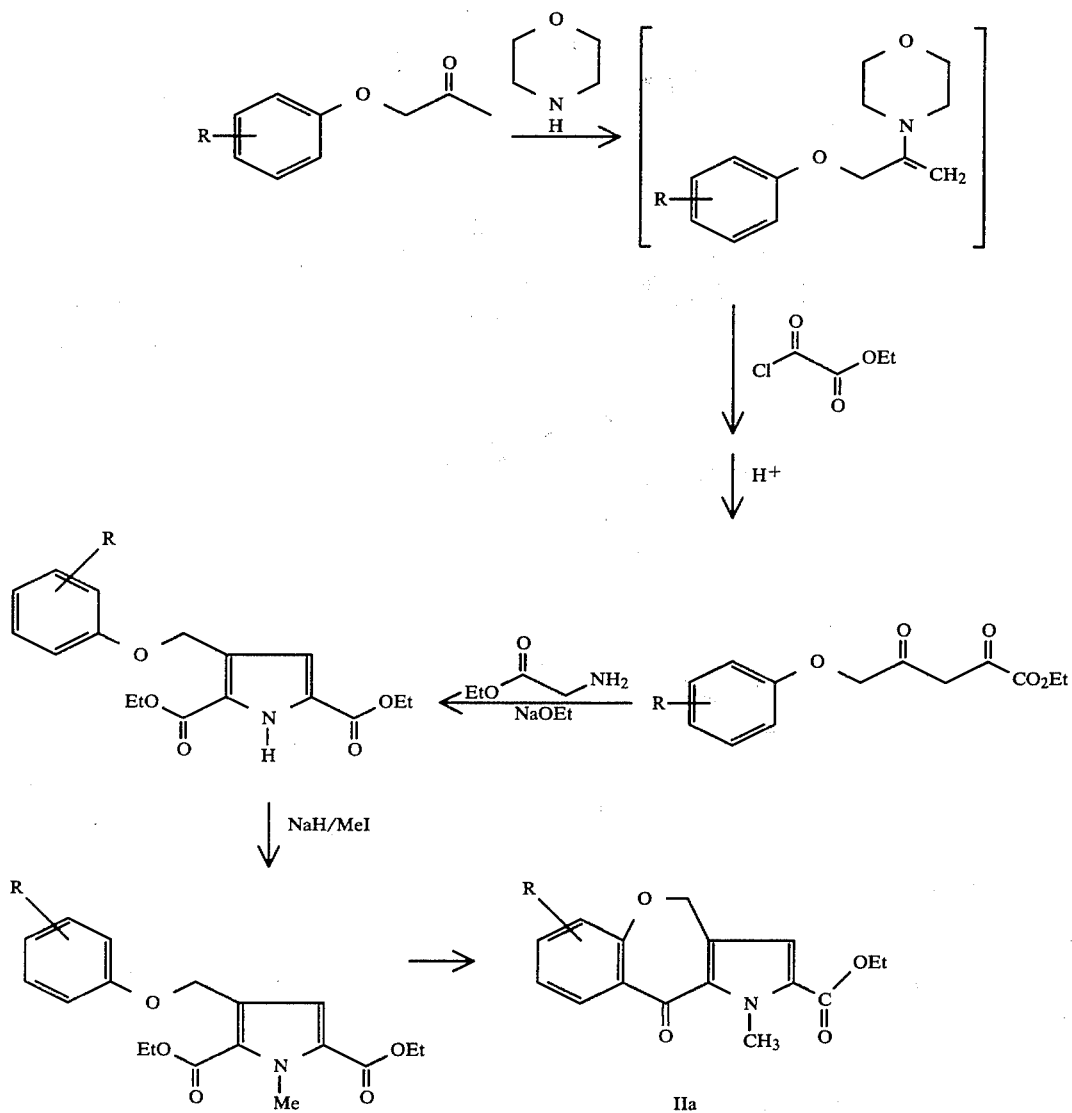
Scheme III
(Illustrated by Example 12)
Et may also be other loweralkyl groups
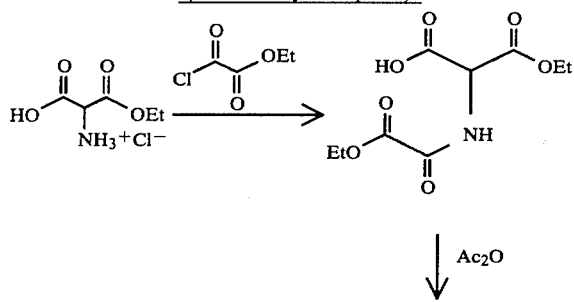
Scheme IV
(Illustrated by Example 13)
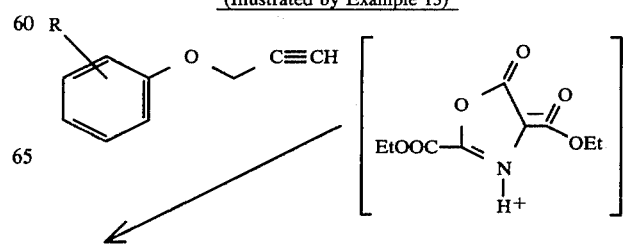
-continued
Scheme IV
(Illustrated by Example 13)

-continued
Scheme IV
(Illustrated by Example 13)

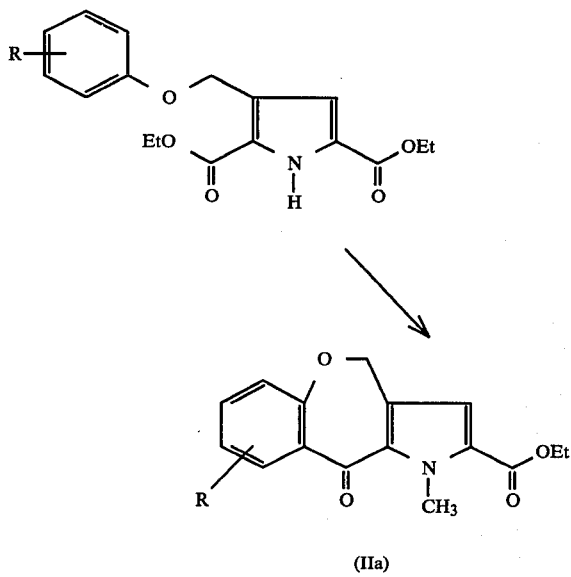

(IIa)

Note: Et may also be other loweralkyl groups.

Scheme V
(Illustrated by Example 14)

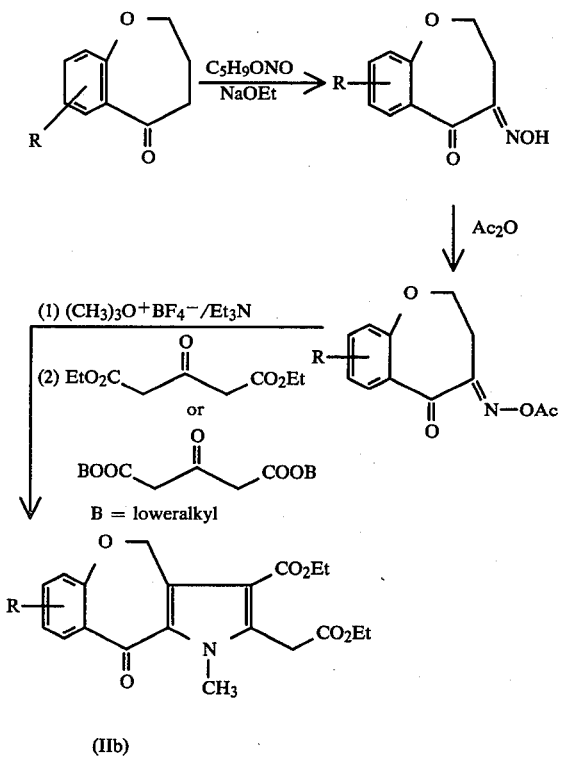

(IIb)

Note: Et may also be other loweralkyl groups.

The pharmaceutically acceptable salts of the acids of Formula I are readily prepared by conventional procedures well-known in the art. For example, an acid of formula I is treated with an appropriate amount of a base, such as an alkali or alkaline earth metal hydroxide, e.g. sodium hydroxide, potassium hydroxide, calcium hydroxide, or an organic base such as an amine, e.g., dibenzylethylenediamine, trimethiamine piperdine, pyrrolidine, benzylamine and the like.

EXAMPLE 1

5,10-Dihydro-1-methyl-10-oxo-1H-[a]benzoxepino[4,3-b]pyrrole-2-acetic acid

Step 1: Preparation of Diethyl 3-[N-methyl N-carbethoxymethyl]pent-2-endioate

Diethyl 3-[diethylphosphoryloxy]pent-2-endioate (50.25 g, 0.15 mol) is placed in a one liter flask along with absolute ethanol (275 ml). Sarcosine ethyl ester hydrochloride (34.4 g, 0.225 mol) is added, and the heterogeneous mixture is stirred for five minutes. Triethylamine (27.6 ml, 0.20 mol) is then added over 10 minutes. Solids begin to form soon after addition commences. The mixture is allowed to stir at room temperature for 16 hours. Then the reaction mixture is poured into a four liter separatory funnel containing ether (1500 ml). The organic solution is extracted with water (3×500 ml), brine (200 ml) and dried over sodium sulfate. The solvent is then removed to give 42.4 g of yellow oil. The oil is purified using preparative HPLC (high-pressure liquid chromatography with 3:1/hexane:ethyl acetate as eluant) to give 24.4 g (55%) of diethyl 3-[N-methyl N-carbethoxymethyl]pent-2-endioate.

Step 2: Preparation of Ethyl 3-ethoxycarbonyl-4-hydroxy-1-methylpyrrole-2-acetate Diethyl 3-[N-methyl-N-carbethoxymethyl]pent-2-endioate (10.0 g, 33.2 mmol) is placed in a 25 ml recovery flask with boiling chips and an alembic stillhead is attached. The flask is evacuated to 100 mm Hg and the flask is immersed in an oil bath heated to 180°. After a few minutes, ethanol begins to condense in the alembic. Heating is maintained for an additional 15 minutes. The vacuum is then reduced to 0.1 mm Hg. The ethanol evaporates and a light yellow oil distills into the alembic. When distillation is complete, the system is cooled. The oily product solidifies. The product is transferred to a 25 ml recovery flask (under $N_2$) and recrystallized from ethanol to give 3.57 g of product as a first crop (M.P. 100°-1°). The mother liquor is concentrated to give an additional 2.60 g of material; total yield 6.17 g (73%). The air-sensitive product is stored in the cold under nitrogen and is used directly in the next step without further purification.

Step 3: Preparation of Ethyl 5-[o-(chloromethyl)benzoyl]-3-ethoxycarbonyl-4-hydroxy-1-methylpyrrole-2-acetate Ethyl 3-ethoxycarbonyl-4-hydroxy-1-methylpyrrole-2-acetate (510 mg, 2.0 mmol) is mixed with o-(chloromethyl)benzoyl chloride (565 μl, 4.0 mmol) under nitrogen, and 2.0 ml anhydrous trifluoromethanesulfonic acid is added. The reaction mixture is stirred at room temperature for one hour followed by dilution with methylene chloride (50 ml), and then water (30 ml). Solid sodium bicarbonate is slowly added until the acid is neutralized. The organic layer is separated and the aqueous layer is washed with methylene chloride (50 ml). The combined organic layers are washed with water (20 ml) and saturated brine (50 ml). Subsequently, the washed layers are dried with sodium sulfate and the solvent is removed in vacuo to give a red solid which is recrystallized from ethanol to give 525 mg (64.5%) of ethyl 5-[o-(chloromethyl)benzoyl]-3-ethoxycarbonyl-4-hydroxy-1-methylpyrrole-2-acetate.

Step 4: Preparation of Ethyl 5,10-dihydro-3-ethoxycarbonyl-1-methyl-10-oxo-1H-[2]benzoxepino[4,3-b]-pyrrole-2-acetate Ethyl 5-[o-(chloromethyl)benzoyl]-3-ethoxycarbonyl-4-hydroxy-1-methylpyrrole-2-acetate (525 mg, 1.29 mmol) is suspended in 5 ml dry DMF under nitrogen followed by subsequent addition of sodium hydride (68 mg, 1.42 mmol, 50% dispersion in oil). Gas is evolved and the reaction turns dark brown. The mixture is stirred for one hour, then the solution is poured into water (50 ml). Upon agitation, a solid separates which is filtered and dried. The crude material is recrystallized from ethanol to give 426 mg (90%) of ethyl 5,10-dihydro-3-ethoxycarbonyl-1-methyl-10-oxo-1H-[2]benzoxepino[4,3-b]pyrrole-2-acetate.

Step 5: Preparation of 5,10-Dihydro-3-hydroxycarbonyl-1-methyl-10-oxo-1H-[2]benzoxepino[4,3-b]-pyrrole-2-acetic acid Ethyl 5,10 dihydro-3-ethoxycarbonyl-1-methyl-10-oxo-1H-[2]benzoxepino[4,3-6]pyrrole-2-acetate (426 mg, 1.14 mmol) is placed in a 25 ml recovery flask. Ethanol (2 ml) is added followed by 2.5 N aqueous sodium hydroxide (5 ml, 12.5 mmol). The mixture is heated to reflux with vigorous stirring, and heating is maintained for one hour after the reaction becomes homogeneous. The solution is then cooled and acidified with 2.5 N aqueous HCl (6 ml). The precipitated solid is filtered and washed with water, then dried in vacuo to give 360 mg (100%) of 5,10 dihydro-3-hydroxycarbonyl-1-methyl-10-oxo-1H-[2]benzoxepino[4,3-b]-pyrrole-2-acetic acid.

Step 6: Preparation of Ethyl 5,10-Dihydro-3-hydroxycarbonyl-1-methyl-10-oxo-1H-[2]benzoxepino[4,3-b]-pyrrole-2-acetate 5,10-Dihydro-3-hydroxycarbonyl-1-methyl-10-oxo-1H-[2]benzoxepino[4,3-b]pyrrole-2-acetic acid (360 mg, 1.14 mmol) is suspended in absolute ethanol (5 ml) and heated to reflux under nitrogen. Then concentrated HCl (75 µl) is added, and the mixture is heated at reflux for 30 minutes. The homogeneous solution is allowed to cool, and the product crystallizes. The solid is filtered and washed with ice-cold ethanol and dried to give 350 mg (89%) of ethyl 5,10-dihydro-3-hydroxycarbonyl-1-methyl-10-oxo-1H-[2]benzoxepino[4,3-b]pyrrole-2-acetate. M.P. 201°–202° (dec).

Step 7: Preparation of Ethyl 5,10-dihydro-1-methyl-10-oxo-1H-[2]benzoxepino[4,3-b]pyrrole-2-acetate Ethyl 5,10-dihydro-3-hydroxycarbonyl-1-methyl-10-oxo-1H-[2]benzoxepino[4,3-b]pyrrole-2-acetate (350 mg, 1.02 mmol) is placed in a 10 ml recovery flask and the flask is purged 10 times with nitrogen. The flask is then heated to 210°. The solid melts and gas is evolved. Heating is continued until gas evolution ceases, then the reaction is cooled to give an orange glass. The product is purified by preparative TLC on silica gel in 2:1 hexanes:ethyl acetate and the material removed to give 200 mg (66%) of oily ethyl 5,10-dihydro-1-methyl-10-oxo-1H-[2]benzoxepino[4,3-b]pyrrole-2-acetate.

Step 8: Preparation of 5,10-Dihydro-1-methyl-10-oxo-1H-[2]benzoxepino[4,3-b]pyrrole-2-acetic acid Ethyl 5,10-dihydro-1-methyl-10-oxo-1H-[2]benzoxepino[4,3-b]pyrrole-2-acetate (196 mg, 0.66 mmol) is dissolved in ethanol and 2.5 N aqueous sodium hydroxide (2 ml, 5 mmol) is added dropwise at reflux under nitrogen. The reaction is heated for an additional ten minutes, then the solution is cooled and diluted with water (5 ml). The resulting mixture is acidified with 2.5 N aqueous HCl (3 ml). The product separates as an oil, then solidifies on scratching. The solid is filtered, washed with water and dried to give 160 ml crude product. The product is recrystallized from ethanol to give 102 mg of 5,10-dihydro-1-methyl-10-oxo-1H-[2]benzoxepino[4,3-b]pyrrole-2-acetic acid, M.P. 114°–116° (dec).

EXAMPLE 2

7-Chloro-4,10-dihydro-1-methyl-10-oxo-1H-[1]benzoxepino[4,3-b]-2-acetic acid

Step 1: Preparation of Ethyl-1,4 dimethyl-5-ethoxycarbonylpyrrole-2-acetate

Ethyl 5-chlorocarbonyl-1,4 dimethylpyrrole-2-acetate (29.3 g, 0.12 mol, prepared acc. to U.S. Pat. No. 3,950,355) is dissolved in 150 ml of 1:1 methylene chloride/ether and added over 10 minutes to a solution of pyridine (15 ml) and absolute ethanol (20 ml) in ether (100 ml) with stirring. After addition is complete, 4-N,N-dimethylaminopyridine (300 mg) is added. Stirring is continued for three hours. Ether (250 ml) is then added and deposited solids are removed by filtration. The organic solution is washed with aqueous 1 N HCl (2×100 ml), then brine (100 ml), and the ether layer is dried with magnesium sulfate. The solvent is then removed to give 26.3 g (87%) of ethyl-1,4 dimethyl-5-ethoxycarbonylpyrrole-2-acetate as a low melting red solid.

Step 2: Preparation of Ethyl 1,4-dimethyl-5-ethoxycarbonyl-α-oxopyrrole-2-acetate Ethyl-1,4 dimethyl-5-ethoxycarbonylpyrrole-2-acetate (26.3 g, 0.104 mol) is mixed with triethylamine (7.2 ml, 0.052 mol), pyridine (165 ml, dried over 4 A sieves) and selenium dioxide (12.9 g, 0.115 mol) under nitrogen. The mixture is stirred mechanically and is heated to 95°–100° for 6.5 hours. The reaction is then allowed to cool and the heterogeneous mixture is filtered through a bed of Celite and washed with ether until no further color comes through. The organic solution is then washed with 2 N HCl (4×200 ml), and the combined acid washes are backwashed with ether (150 ml). The combined ether layers are washed with saturated aqueous sodium bicarbonate (100 ml) and saturated brine (150 ml). The ether solution is dried over sodium sulfate and the solvent is removed to give a brown oil which crystallizes on standing. The product is purified by preparative HPLC (4/1 hexanes/ether) to give 14.5 g of ethyl 1,4-dimethyl-5-ethoxycarbonyl-α-oxopyrrole-2-acetate.

Step 3: Preparation of Ethyl 4-bromomethyl-5-ethoxycarbonyl-1-methyl-α-oxo-pyrrole-2-acetate Ethyl-1,4-dimethyl-5-ethoxycarbonyl-α-oxopyrrole-2-acetate (14.79 g, 55.5 mmol) is dissolved in carbon tetrachloride (300 ml) and placed in a 500 ml round bottom flask. Then N-bromosuccinimide (11.1 g, 62.5 mmol) is added, a reflux condenser is attached and the system is flushed with nitrogen. The mixture is slowly stirred. A 120 V, 150 W G.E. projection lamp is placed against the side of the flask and the lamp and the flask are enclosed in aluminum foil. The reaction mixture is then irradiated for one hour. The lamp is then removed, the solution is cooled and the succinimide is filtered off. The solvent is removed to give a yellow oil which solidifies. This material is then used immediately in the next reaction (vide infra).

Step 4: Preparation of Ethyl 4-(m-chlorophenoxy)-methyl-5-ethoxycarbonyl-1-methyl-α-oxopyrrole-2-acetate Crude ethyl-4-bromomethyl-5-ethoxycarbonyl-α-oxopyrrole-2-acetate (vide supra) is dissolved in dimethylformamide (100 ml) and cooled to 0°. A solution of sodium m-chlorophenoxide (62 mmol; prepared from 1.47 g sodium hydride and 8.0 ml i.e., 65 mmol m-chlorophenol) in dimethylformamide (40 ml) is added dropwise over 10 minutes with cooling. The cooling bath is subsequently removed and stirring is continued for 1.5 hours. The reaction mixture is then poured into water (600 ml) and extracted with ether (3×250 ml). The combined ether layers are washed with water (3×100 ml) followed by saturated brine (2×100 ml). The organic layer is dried over sodium sulfate and the solvent removed to give 23 g crude brown oil. The oil is diluted with ethanol (65 ml) and the product crystallizes. The solid is filtered, washed with cold ethanol, and then dried to give 8.77 g (40%) of ethyl 4-(m-chlorophenoxy)-methyl-5-ethoxycarbonyl-1-methyl-α-oxopyrrole-2-acetate.

Step 5: Preparation of 4-(m-Chlorophenoxy)methyl-5-hydroxycarbonyl-1-methyl-α-oxopyrrole-2-acetic acid Ethyl 4-(m-chlorophenoxy)methyl-5-ethoxycarbonyl-1-methyl-α-oxopyrrole-2-acetate (7.96 g, 21 mmol) is placed in a 100 ml recovery flask and 25 ml 2.5 N aqueous sodium hydroxide (62.5 mmol) are added. The flask is heated with stirring under nitrogen to 74°. Ethanol (4 ml) is added and the solid begins to dissolve. After 15 minutes the reaction is homogeneous. After heating for one hour, the flask is cooled and 2.5 N aqueous HCl (30 ml, 75 mmol) is added slowly to precipitate the diacid. The resulting solid is filtered, washed with $H_2O$, and then dried in vacuo to give 7.0 g of crude 4-(m-chlorophenoxy)methyl-5-hydroxycarbonyl-1-methyl-α-oxopyrrole-2-acetic acid.

Step 6: Preparation of Ethyl 4-(m-chlorophenoxy)-methyl-5-hydroxycarbonyl-1-methyl-α-oxopyrrole-2-acetate 4-(m-Chlorophenoxy)methyl-5-hydroxycarbonyl-1-methyl-α-oxopyrrole-2-acetic acid (5.5 g, 16,3 mmol) is suspended in absolute ethanol (40 ml) and concentrated HCl (1.0 ml) is added. The mixture is heated to reflux for 35 minutes, then cooled and the product crystallizes. The solid is filtered and dried to give 2.51 g (42%) of pure ethyl 4-(m-chlorophenoxy)methyl-5-hydroxycarbonyl-1-methyl-α-oxopyrrole-2-acetate.

Step 7: Preparation of 7-Chloro-4,10-dihydro-1-methyl-10-oxo-1H-[1]benzoxepino[4,3-b]-pyrrole-2-acetic acid Following substantially the same procedure as described in Example 5, infra, steps 4–6, ethyl 4-(m-chloro-phenoxy)methyl-5-hydroxycarbonyl-1-methyl-α-oxopyrrole-2-acetate is converted to 7-chloro-4,10-dihydro-1-methyl-10-oxo-1H-[1]benzoxepino[4,3-b]pyrrole-2-acetic acid

EXAMPLE 3

1,4,5,10,-Tetrahydro-7-chloro-1,α-dimethyl-10-oxobenzocyclohepta[1,2-b]pyrrole-2-acetic acid Step 1: Preparation of t-Butyl 5-(m-chlorophenyl)-3-oxopentanoate Sodium hydride (5.43 g, 0.11 mol, 50% as an oil suspension) is placed in a 500 ml 3-neck flask (equipped with a thermometer, an addition funnel, and a rubber septum) under nitrogen and washed 2×100 ml hexanes to remove the oil. Then 230 ml dry THF (tetrahydrofuran) is introduced and the sodium hydride suspension is cooled to 4° and magnetically stirred. t-butylacetoacetate (16.5 ml, 0.1 mol) is added with a rate which is controlled so that the gas evolution is not too vigorous and the temperature is maintained at less than 10°. Stirring is continued until gas evolution ceases (1 hr). Then 62 ml of 1.7 M BuLi in hexane (0.105 mol) is added via syringe at a rate such that the temperature does not rise above 10°. The initial orange color becomes red during addition, but turns into pink after addition is complete. A fine solid also separates from solution. The resulting mixture is stirred for an additional 15 min. before 15.0 ml m-chlorobenzyl chloride (20.0 g, 0.125 mol) in 20 ml dry THF is added dropwise at a rate such that the temperature is maintained between 9° and 12°. When addition is complete, the cooling bath is removed and the reaction is stirred for an additional 1 hr. The reaction mixture is then poured into a 2 l Erlenmeyer flask and 300 ml diethyl ether is added followed by the addition of 130 ml cold 3 N aqueous HCl with stirring. The mixture is stirred for 15 min, and the layers are separated, and the acid layer is washed twice with 150 ml diethyl ether. The combined organic layers are then washed twice with 200 ml of water, 2×100 ml of aqueous 1% Citric acid (pH 4.5), and finally with 100 ml saturated aqueous brine. The organic layer is dried with anhydrous sodium sulfate and the solvent removed to give 24.5 g of t-butyl 5-(m-chlorophenyl)-3-oxo-pentanoate.

Anal. calc. for $C_{15}H_{19}ClO_3$: C, 63.72; H, 6.77; Cl, 12,54. Found: C, 63.67; H, 6.70; Cl, 12.71.

Step 2: Preparation of t-Butyl 5-(m-chlorophenyl)-2-hydroximino-3-oxopentanoate

Crude t-butyl 5-(m-chlorophenyl)-3-oxopentanoate (24.5 g, vide supra) is dissolved in 15 ml glacial acetic acid and is added to a 250 ml 3-neck flask equipped with a thermometer, a mechanical stirrer and an addition funnel. The solution is stirred and cooled to 3°. Then a solution of 6.9 g sodium nitrite (0.1 mol) in 20 ml water is added dropwise at a rate such that the internal temperature is held between 5°–7° with cooling. After addition is complete, the reaction is vigorously stirred for 30 minutes at 10°. A solution of 8 g KCl in 40 ml water is added all at once and the mixture is stirred an additional 30 minutes with ice bath cooling, then 15 minutes more without cooling. The resulting reaction mixture is extracted twice with 150 ml diethyl ether, and the ether extracts are combined and washed 3×100 ml water, 100 ml of saturated aqueous brine, and the organic layer is then dried with anhydrous sodium sulfate and the solvent removed to give 23.2 g yellow oil which contains 10% (m-chloro)benzyl chloride and 90% of t-Butyl 5-(m-chloro-phenyl)-2-hydroximino-3-oxopentanoate by NMR spectroscopy. The oil slowly solidifies on standing, and is used in the next step without further purification.

Step 3: Preparation of Ethyl 5-(t-butoxycarbonyl)-4-[2-(m-chlorophenyl)ethyl]-3-ethoxycarbonylpyrrole-2-acetate Crude t-butyl 5-(m-chlorophenyl)-2-hydroximino-3-oxopentanoate (43 g., 0.15 mol) and diethyl acetonedicarboxylate (28 ml, 30.3 g, 0.15 mol) are placed in a 1 liter round bottom flask and 250 ml of glacial acetic acid added. With stirring, 25 g (0.30 mol) anhydrous sodium acetate is added followed by 26 g Zn dust (94% fine, 0.364 mol) in a portionwise manner so that the exotherm does not bring the reaction to reflux. When addition is complete, the reaction is heated on a steam bath for one hour. The hot solution is then decanted from the residual zinc into 3 liters of ice water, and the resulting mixture is stirred vigorously until the oil solidifies. The mixture is then allowed to stand for 1.5 hours, and the solid is filtered. The solid is washed with water, dried in vacuo and recrystallized to give 21.5 g (31%) of ethyl 5-(t-butoxycarbonyl)-4-[2-(m-chlorophenyl)ethyl]-3-ethoxycarbonylpyrrole-2-acetate, M.P. 131°–132°.

Anal. calc. for $C_{24}H_{30}NClO_6$: C, 62.13; H, 6.52; N, 3.02; Cl, 7.64. Found: C, 62.31; H, 6,61; N, 3.08; Cl, 7.55.

Step 4: Preparation of Ethyl 5-(t-butoxycarbonyl)-4-[2-(m-chlorophenyl)ethyl]-3-ethoxycarbonyl-1-methyl-pyrrole-2-acetate Sodium hydride (2.23 g, 0.0465 mol, 50% dispersion in oil) is placed in a 500 ml round bottom flask under nitrogen and washed with 100 ml hexanes. Dry DMF (225 ml) is added, followed by 21.5 g ethyl 5-(t-butoxycarbonyl)-4-[2-(m-chlorophenyl)ethyl]-3-ethoxycarbonylpyrrole-2-acetate portionwise in such a way that the gas evolution does not become excessive. After addition is complete, the solution is stirred until gas evolution ceases. Then 4.4 ml (0.0475 mol) dimethyl sulfate is added via syringe. The resulting solution is stirred for two hours before it is poured into 1.5 liters of water. The aqueous suspension is extracted with $3 \times 500$ ml of ether, the combined ether layers are washed $4 \times 150$ ml water, 200 ml saturated aqueous brine, and dried with sodium sulfate. The solvent is removed to give 22.1 g (99%) of ethyl 5-(t-butoxycarbonyl)-4-[2-(m-chlorophenyl)ethyl]-3-ethoxycarbonyl-1-methyl-pyrrole-2-acetate that is pure by NMR spectroscopy.

Step 5: Preparation of Ethyl 4-[2-(m-chlorophenyl)ethyl]-3-ethoxycarbonyl-1-methylpyrrole-2-acetate Ethyl 5-(t-butoxycarbonyl)-4-[2-(m-chlorophenyl)ethyl]-3-ethoxycarbonyl-1-methylpyrrole-2-acetate (22.1 g, 0.0465 mol) is dissolved in 80% aqueous TFA (100 ml) at 0°. After the cooling bath is removed, the moisture is stirred at room temperature for 1 hour. The solvent is then removed in vacuo to give a red oil which solidifies on standing to affore 17.2 g (99%) of ethyl-4-[2-(m-chlorophenyl)ethyl]-3-ethoxycarbonyl-1-methyl-pyrrole-2-acetate.

Step 6: Preparation of Ethyl 5-chlorocarbonyl-4-[2-(m-chlorophenyl)ethyl]-3-ethoxycarbonyl-1-methyl-pyrrole-2-acetate Ethyl-4-[2-(m-chlorophenyl)ethyl]-3-ethoxycarbonyl-1-methylpyrrole-2-acetate (2.50 g, 5.7 mmol) is dissolved in methylene chloride (5 ml) and placed in a resealable sealed tube. The tube is cooled to 0° and phosgene (2 ml) is condensed into it. The tube is then sealed and heated to 60°. After 16 hours, the tube is again cooled to 0° and opened. The cooling bath is removed, and a boiling chip is added to the opened tube. The tube is allowed to stand at ambient temperature until phosgene evolution ceases. The remaining solvents are then removed in vacuo to give a red solid. The crude product can be recrystallized from hexane/methylene chloride/ethyl acetate to give a white solid (1.45 g). An additional 370 mg can be obtained by concentrating the mother liquor to give a combined yield of 1.82 g (71%) of ethyl-5-chlorocarbonyl-4-[2-(m-chlorophenyl)ethyl]-3-ethoxycarbonyl-1-methylpyrrole-2-acetate.

Step 7: Preparation of Ethyl 1,4,5,10 tetrahydro-7-chloro-3-ethoxycarbonyl-1-methyl-10-oxobenzocyclohepta[1,2-b]pyrrole-2-acetate Ethyl-5-chlorocarbonyl-4-[2-(m-chlorophenyl)ethyl]-3-ethoxycarbonyl-1-methylpyrrole-2-acetate (570 mg, 1.3 mmol) is dissolved in 18 ml methylene chloride under nitrogen at room temperature. Aluminum chloride (420 mg, 3.2 mmol) is added all at once. The reaction immediately turns bright yellow. After the mixture is stirred for 2 hours, methylene chloride (10 ml) and water are carefully added and rapid stirring is maintained for five minutes. The organic layer is separated, washed with water (10 ml), aqueous sodium bicarbonate (10 ml), saturated aqueous brine (10 ml) and dried with anhydrous magnesium sulfate. The solvent is removed to give a white solid which is recrystallized from isopropanol to give 420 mg (88%) of ethyl 1,4,5,10-tetrahydro-7-chloro-3-ethoxy-carbonyl-1-methyl-10-oxobenzocyclohepta[1,2-b]pyrrole-2-acetate.

Step 8: Preparation of 1,4,5,10-Tetrahydro-7-chloro-3-hydroxycarbonyl-1-methyl-10-oxobenzocyclohepta[1,2-b]pyrrole-2-acetic acid Ethyl 1,4,5,10-tetrahydro-7-chloro-3-ethoxycarbonyl-1-methyl-10-oxo-benzocyclohepta[1,2-b]-pyrrole-2-acetate (7.87 g, 19.5 mmol) is suspended in ethanol (20 ml) and is heated at reflux. To the resulting mixture is added 2.5 N aqueous sodium hydroxide (20 ml, 50 mmol). The reaction is heated at reflux with stirring for 1 hour after it becomes homogeneous. The solution is cooled and diluted with ice water (150 ml), then acidified to pH 2 with 6 N aqueous HCl. The resulting precipitate is filtered and dried in vacuo to give 5.06 g (75%) of 1,4,5,10-tetrahydro-7-chloro-3-hydroxy-carbonyl-1-methyl-10-oxobenzocyclohepta[1,2-b]pyrrole-2-acetic acid.

Step 9: Preparation of Ethyl 1,4,5,10 tetrahydro-7-chloro-3-hydroxycarbonyl-1-methyl-10-oxobenzocyclo-hepta[1,2-b]pyrrole-2-acetate 1,4,5,10 Tetrahydro-7-chloro-3-hydroxycarbonyl-1-methyl-10-oxobenzocyclohepta[1,2-b]pyrrole-2-acetic acid (5.06 g, 14.6 mmol) is suspended in absolute ethanol (120 ml) and heated at reflux. Then 1.80 ml concentrated aqueous HCl is added and the resulting mixture is heated for 35 minutes. The solution is then allowed to cool and crystals separate out. The solid is collected and dried to give 4.50 g product. An additional 300 mg product is obtained from concentrating the mother liquor to afford a total yield (4.80 g, 88%) of ethyl 1,4,5,10 tetrahydro-7-chloro-3-hydroxycarbonyl-1-methyl-10-oxobenzocyclohepta[1,2-b]pyrrole-2-acetate, M.P. 199°–200° (dec).

Step 10: Preparation of Ethyl 1,4,5,10 tetrahydro-7-chloro-1-methyl-10-oxobenzocyclohepta[1,2-b]pyrrole-2-acetate Ethyl 1,4,5,10-tetrahydro-7-chloro-3-hydroxycarbonyl-1-methyl-10-oxo-benzocyclohepta[1,2-b]pyrrole-2-acetate (4.80 g, 12.5 mmol) is placed in a 50 ml round bottom flask and purged 12 times with nitrogen. Then the flask is immersed in a Wood's metal bath at 215°. Gas is evolved as the solid dissolves. The heating is maintained for two hours, then the flask is cooled. The gummy product is dissolved in ethanol (10 ml), and on scratching, crystals are deposited. The solid is filtered off and dried (2.6 g). On cooling the mother liquors a second crop is obtained (1.0 g). The total yield of ethyl 1,4,5,10 tetrahydro-7-chloro-1-methyl-10-oxobenzocyclohepta[1,2-b]pyrrole-2-acetate is 3.6 g (87%).

Step 11: Preparation of Ethyl 1,4,5,10-tetrahydro-7-chloro-1,α-dimethyl-10-oxobenzocyclohepta [1,2-b]pyrrole-2-acetate Sodium hydride (144 mg, 3.0 mmol as a 50% dispersion in oil) is placed in a 50 ml recovery flask under nitrogen and washed with $2 \times 20$ ml hexanes. Dry DMF (8 ml) is then added, followed by dropwise addition of a solution of 990 mg (3.0 mmol) of ethyl-1,4,5,10-tetrahydro-7-chloro-1-methyl-10-oxobenzocyclohepta[1,2-b]pyrrole-2-acetate in 6 ml dry DMF. The reaction immediately turns cherry redblack. The mixture is stirred for 15 minutes after the addition is complete, then 200 μl (3.2 mmol) methyl iodide is added. Stirring is continued for 25 minutes before the reaction is poured into 75 ml water and the resulting milky solution is extracted with ether (3×50 ml). The combined ether layers are washed with water (2×50 ml), then saturated brine (2×50 ml) and dried with sodium sulfate. The solvent is removed to give an oil which crystallizes on trituration with ethanol. The solid (580 mg) is removed and dried and the residue is chromatographed on silica gel (1/1 ether/hexane) to give an additional 120 mg. Total yield of ethyl 1,4,5,10-tetrahydro-7-chloro-1,α-dimethyl-10-oxobenzocyclohepta[1,2-b]pyrrole-2-acetate is 700 mg (68%).

Step 12: Preparation of 1,4,5,10-Tetrahydro-7-chloro-1,α-dimethyl-10-oxobenzocyclohepta[1,2-b]pyrrole-2-acetic acid Ethyl 1,4,5,10-tetrahydro-7-chloro-1,α-dimethyl-10-oxobenzocyclohepta[1,2-b]pyrrole-2-acetate (1.30 g, 3.78 mmol) is suspended in 10 ml 2.5 N aqueous sodium hydroxide and heated to 100° with stirring. The solid dissolves after about 15 minutes. After 25 minutes, the solution is cooled and acidified with 13 ml 2.5 N aqueous HCl. The resulting solid is filtered off and recrystallized from ethanol to give 772 mg (65%) of 1,4,5,10-tetrahydro-7-chloro-1,α-diemthyl-10-oxo-benzocyclohepta[1,2-b]pyrrole-2-acetic acid, M.P. 171°–172° (dec).

EXAMPLE 4

7-Chloro-1-methyl-10H-10-oxo-benzocycloheptena[1,2-b]pyrrole-2-acetic acid

Step 1: Preparation of Ethyl 7-chloro-3-ethoxycarbonyl-1-methyl-10H-10-oxo-benzocycloheptena[1,2-b]pyrrole-2-acetate Ethyl 1,4,5,10-tetrahydro-7-chloro-3-ethoxycarbonyl-1-methyl-10-oxobenzocyclohepta[1,2-b]pyrrole-2-acetate (390 mg, 0.95 mmol) and 2,3-dichloro-5,6-dicyano-1,4-benzoquinone (454 mg. 2.0 mmol) are suspended in dioxane (1.0 ml) and heated to 108° for 110 hours. The reaction is then cooled, diluted with methylene chloride (40 ml), washed with water (2×20 ml), 50% saturated aqueous sodium bicarbonate (20 ml) and saturated brine (20 ml). The organic layer is dried with magnesium sulfate and the solvent is removed to give a crude solid which is recrystallized from ethanol to give 205 mg pure ethyl 7-chloro-3-ethoxy-carbonyl-1-methyl-10H-10-oxo-benzocycloheptena[1,2-b]pyrrole-2-acetate (65.5%).

Step 2: Preparation of 7-Chloro-3-hydroxycarbonyl-1-methyl-10H-10-oxo-benzocycloheptenan-[1,2-b]pyrrole-2-acetic acid Ethyl-7-chloro-3-ethoxycarbonyl-1-methyl-10H-10-oxo-benzocycloheptena[1,2-b]pyrrole-2-acetate (392 mg, 0.98 mmol) is suspended in ethanol (4 ml) and heated to reflux, then 2.5 N aqueous sodium hydroxide (2.0 ml, 5.0 mmol) is added dropwise. The heterogeneous solution is stirred at reflux until all of the solid dissolves, then an additional 30 minutes more. The solution is cooled, and water (3 ml) is added, followed by 2.5 N aqueous HCl (2.5 ml, 6.25 mmol) to give a milky suspension. This suspension is vigorously stirred for 30 minutes at 0°, then two hours at room temperature. The result is a filterable solid which is washed with water and dried in vacuo to give 320 mg (95%) of pure 7-Chloro-3-hydroxycarbonyl-1-methyl-10H-10-oxo-benzocycloheptena[1,2-b]pyrrole-2-acetic acid.

Step 3: Preparation of 7-Chloro-1-methyl-10H-10-oxo-benzocycloheptena[1,2-b]pyrrole-2-acetic acid 7-Chloro-3-hydroxycarbonyl-1-methyl-10-oxo-10H-benzocycloheptena[1,2-b]pyrrole-2-acetic acid (120 mg, 0.29 mmol) is suspended in anhydrous trifluoroacetic acid (10 ml) and heated to reflux. After four hours, all of the solid finally dissolves. Heating is continued for an additional one hour, then the reaction is cooled and the solvent is removed in vacuo. The residue is treated with water (10 ml) and the resulting solids are filtered, washed with water, and dried in vacuo to give 103 mg (97%) of pure 7-chloro-1-methyl-10H-10-oxo-benzocycloheptena-[1,2-b]pyrrole-2-acetic acid, M.P. 220° (dec).

EXAMPLE 5

7-Chloro-4,10-dihydro-1-methyl-10-oxo-1H-[1]benzothiepino[4,3-b]pyrrole-2-acetic acid Step 1: Preparation of Ethyl 4-(m-chlorophenylthio)-methyl-5-ethoxycarbonyl-1-methyl-α-oxo-pyrrole-2-acetate Ethyl 1,4-dimethyl-5-ethoxycarbonyl-α-oxopyrrole-2-acetate (2.70 g, 10.0 mmol) is dissolved in carbon tetrachloride (55 ml) and N-bromosuccinimide (2.0 g, 11.3 mmol) is added. The system is purged with nitrogen, a reflux condenser is attached, and the reaction is irradiated with slow stirring with a 150 W 120 V projection lamp for one hour. The reaction is then cooled, the solids are filtered off, and the solvent removed to give the crude 4-bromomethylpyrrole as an oil which solidifies. This solid is dissolved in dry dimethylformamide (15 ml) and cooled to 0° under nitrogen. To this solution is added dropwise a solution of sodium thiophenoxide (11 mmols) in dimethylformamide (20 ml; prepared by the reaction of 11 mmols of sodium hydride with 12 mmols of m-chlorothiophenol in DMF) over thirty minutes. When addition is complete, the cooling bath is removed and the solution is stirred for 1.5 hours at room temperature. The reaction mixture is poured into water (200 ml) and the resulting milky solution is extracted with ether (3×100 ml). The combined ether layers are washed with water (3×50 ml), then brine (100 ml) and dried with sodium sulfate. The solvent is removed to give a brown oil. The oil is dissolved in ethanol (10 ml) and, with scratching, crystals are deposited. The solid is filtered and dried to give 1.28 g (31%) of ethyl 4-(m-chlorophenylthio)methyl-5-ethoxycarbonyl-1-methyl-α-oxopyrrole-2-acetate.

Step 2: Preparation of 4-(m-chlorophenylthio)methyl-5-hydroxycarbonyl-1-methyl-α-oxopyrrole-2-acetic acid Ethyl 4(m-chlorophenylthio)methyl-5-ethoxycarbonyl-1-methyl-α-oxopyrrole-2-acetate (1.28 g, 3.1 mmol) is dissolved in refluxing ethanol (10 ml) and 2.5 N aqueous sodium hydroxide (9 ml, 22.5 mmol) is added. The mixture is heated at reflux for 1.5 hours after the solution becomes homogeneous, then it is cooled in ice and acidified to pH 2.0 with 6 N aqueous HCl. The resulting solid is collected, filtered and dried to give 1.00 g of 4-(m-chlorophenylthio)methyl-5-hydroxycarbonyl-1-methyl-α-oxopyrrole-2-acetic acid.

Step 3: Preparation of Ethyl 4-(m-chlorophenylthio)-methyl-5-hydroxycarbonyl-1-methyl-α-oxo-pyrrole-2-acetate 4-(m-Chlorophenylthio)methyl-5-hydroxycarbonyl-1-methyl-α-oxopyrrole-2-acetic acid (1.0 g, 2.82 mmol) is dissolved in hot ethanol (7 ml) and concentrated HCl (150 μl) is added. The reaction is heated to reflux for 30 minutes, then the mixture is cooled, the solvent is removed in vacuo to give a red oill whih solidifies on standing. The solid is recrystallized from cyclohexane:-chloroform to give 395 mg purple solid, i.e. ethyl 4-(m-chlorophenylthio)methyl-5-hydroxycarbonyl-1-methyl-α-oxo-pyrrole-2-acetate (36%).

Step 4: Preparation of Ethyl 7-chloro-4,10-dihydro-10,α-dioxo-1-methyl-1H-[1]benzothiepino-[4,3-b]pyrrole-2-acetate Ethyl-4-(m-chlorophenylthio)methyl-5-hydroxycarbonyl-1-methyl-α-oxopyrrole-2-acetate (395 mg, 1.02 mmol) is suspended in methylene chloride (4 ml) and oxalyl chloride (175 μl, 2.0 mmol) is added, followed by dimethylformamide (3 μl). The resulting mixture is stirred at room temperature until it becomes homogeneous and gas evolution ceases. The solvent is then removed to give a red oil which is redissolved in methylene chloride (4 ml) and anhydrous stannic chloride (350 μl, 3.0 mmol) added. The reaction mixture is stirred at room temperature for two hours, then the solution is diluted with methylene chloride (11 ml), washed with water (2×5 ml) and saturated brine (5 ml). The organic layer is dried with sodium sulfate and the solvent removed to give 300 mg residue which is purified by preparative TLC (silica gel, 1/1 EtOAc/Hex; Rf 0.75) and recrystallization from ethanol to yield 87 mg (23%) of pure ethyl 7-chloro-4,10-dihydro-10,α-dioxo-1-methyl-1H-[1]benzothiepino-[4,3-b]pyrrole-2-acetate.

Step 5: Preparation of Ethyl 7-chloro-4,10-dihydro-1-methyl-10-oxo-1H-[1]benzothiepino[4,3-b]pyrrole-2-acetate Ethyl 7-chloro-4,10-dihydro-10,α-dioxo-1-methyl-1H-[1]benzothiepino[4,3-b]pyrrole-2-acetate (87 mg, 0.23 mmol) is dissolved in pyridine (2 ml) and placed in a resealable pressure tube along with imidazole (100 mg) and a small stirring bar. The tube and its contents are cooled to −78° and hydrogen sulfide (0.5 ml) is conducted inside it. The tube is then sealed and allowed to come to room temperature with stirring. The mixture is stirred for three hours, then cooled again to −78° and the tube is opened. The tube is allowed to warm and the hydrogen sulfide evaporates. When bubbling ceases, the tube contents are poured into 1.2 N aqueous HCl (30 ml), and the resulting heterogeneous mixture is extracted with ether (2×50 ml). The combined ether layers are washed with 10% aqueous sodium carbonate (3×15 ml), saturated aqueous brine (15 ml), and dried with sodium sulfate. The solvent is removed to give a white solid smelling like garlic. This material is purified by preparative TLC (1/1 EtoAc/Hex, silica gel 0.70) to give 73 mg of ethyl 7-chloro-4,10-dihydro-1-methyl-10-oxo-1H-[1]benzothiepino[4,3-b]pyrrole-2-acetate (88%).

Step 6: Preparation of 7-Chloro-4,10 dihydro-1-methyl-10-oxo-1H-[1]benzothiepino [4,3-b]pyrrole-2-acetic acid Ethyl 7-chloro-4,10 dihydro-1-methyl-10-oxo-1H-[1]benzothiepino[4,3-b]pyrrole-2-acetate (73 mg, 0.21 mmol) is dissolved in hot ethanol (2 ml) and 2.5 N aqueous sodium hydroxide (1 ml, 2.5 mmol) is added. The mixture is heated to 70° and stirred until it becomes homogeneous. Stirring is continued an additional fifteen minutes, then the mixture is cooled and treated with 2.5 N aqueous HCl (1.5 ml) to precipitate 58 mg (86%) of 7-chloro-4,10 dihydro-1-methyl-10-oxo-1H-[1]benzothiepino [4,3-b]pyrrole-2-acetic acid, m.p. 202° (dec).

EXAMPLE 6

4,10-Dioxo-1-methyl-1,4,5,10-tetrahydro-1H-[1]benzaepino[4,3-b]pyrrole-2-acetic acid Step 1: Preparation of Ethyl 1,3-dimethyl-2-(2-nitrobenzoyl)-pyrrole-5-acetate A solution of 5.7 g (0.032 mole) of ethyl 1,4-dimethylpyrrole-2-acetate and 7.0 g (0.038 mole) of 2-nitrobenzoyl chloride in 130 ml xylene is heated at reflux under nitrogen for 18 hours. The mixture is stirred vigorously over a saturated sodium bicarbonate solution for 3 hours at room temperature. The xylene layer is separated from the aqueous layer, washed with brine, dried and filtered. The filtrate is concentrated in vacuo to give 9.9 g (95%) crude ethyl 1,3-dimethyl-2-(2-nitrobenzoyl)-pyrrole-5-acetate which can be used without further purification in the next step.

Step 2: Preparation of Ethyl 1,3-dimethyl-2-(2-nitrobenzoyl)-α-oxo-pyrrole-5-acetate Ethyl 1,3-dimethyl-2-(2-nitrobenzoyl)pyrrole-5-acetate (09.9 g, 0.030 mole) is combined with 3.7 g (0.033 mole) selenium dioxide, 1.5 g (0.015 mole) triethylamine, 48 ml pyridine and warmed under nitrogen in a 90° C. oil bath with stirring for 6.5 hours. The reaction mixture is filtered through Celite, the filtrate diluted with ether and washed with 2.5 N hydrochloric acid and cold water. Drying, filtration, removal of solvent in vacuo and chromatography gives 5.2 g (50% yield) of yellow crystalline ethyl 1,3-dimethyl-2-(2-nitrobenzoyl)pyrrole-α-oxo-5-acetate, m.p. 137.5°–139.5° C.

Analysis: Calcd. for $C_{17}H_{16}N_2O_6$: C, 59.30; H, 4.68; N, 8.14%. Found: C, 59.26; H, 4.80; N, 8.24%.

Step 3: Preparation of Ethyl 3-carbomethoxy-1-methyl-2-(2-nitrobenzoyl)-α-oxo-pyrrole-5-acetate To a refluxing solution of 5.1 g (0.015 mole) ethyl-1,3-dimethyl-2-(2-nitrobenzoyl)-pyrrole-5-glyoxalate in 200 ml carbon tetrachloride is added 1 equivalent (2.6 g) of N-bromosuccinimide and 0.19 g benzoyl peroxide. At hourly intervals thereafter, additional 2.6 g portions of N-bromosuccinimide are added to the refluxing solution until a total of 7.8 g (0.045 mole) is added. The reaction is refluxed an addition 2.5 hours, filtered, diluted with ether and washed with 2.5 N NaOH solution then brine, dried, filtered and concentrated in vacuo to 4.9 g of an orange brominated mixture which is dissolved in 150 ml acetone and treated with a warm (ca. 50° C.) solution of 7.3 g (0.046 mole) potassium permanganate in 150 ml water. The reaction temperature is maintained at 50° C. (±1° C.) for 2 hours before it is acidified by addition of 90 ml 2.5 N HCl and triturated to colorlessness with saturated aqueous sodium sulfite solution. The colorless solution is thoroughly extracted with ethyl acetate and the combined extracts washed with brine, dried and concentrated in vacuo to give 3.1 g dark oil which is dissolved in 100 ml ether and treated for 1.5 hours at room temperature with diazomethane generated from 3.0 g of N-nitrosomethylurea. Glacial acetic acid (5 ml) is added to the reaction mixture (resulting in vigorous gas evolution indicating an excess of diazomethane) and the solution is washed with saturated sodiun bicarbonate solution and brine. Drying, filtration, removal of solvent in vacuo and chromatography gives 1.8 g (0.0046 mole, 31% yield) of ethyl 3-carbomethoxy-1- methyl-2-(2-nitrobenzoyl)-α-oxo-pyrrole-5-acetate as a yellow oil.

Step 4: Preparation of Ethyl 2-(2-aminobenzoyl)-3-carbomethoxy-1-methyl-α-oxo-pyrrole-5-acetate A solution of 1.8 g (0.0046 mole) of ethyl 3-carbomethoxy-1-methyl-2-(2-nitrobenzoyl)-α-oxo-pyrrole-5-acetate in 20 ml. ethyl acetate containing 0.3 g 10% palladium-on-carbon catalyst is hydrogenated in a Parr shaker at 40 p.s.i.g. for 2 hours. The catalyst is filtered off and the solvent evaporated in vacuo to give 1.6 g (97% yield) of a yellow oil, ethyl 2-(2-aminobenzoyl)-3-carbomethoxy-1-methyl-α-oxo-pyrrole-5-acetate.

Step 5: Preparation of Ethyl 4,10-dioxo-1-methyl-1,4,5,10-tetrahydro-1H-[1]-benzazepino[4,3-b]-α-oxo-pyrrole-2-acetate A solution of 1.6 g (0.0045 mole) of ethyl 2-(2-aminobenzoyl)-3-carbomethoxy-1-methyl-α-oxo-pyrrole-5-acetate in 100 ml of anhydrous 1,2-dichloroethane containing 0.086 g p-toluenesulfonic acid is heated to reflux for 22 hours. The solution is diluted with ethyl acetate and washed successively with 2.5 N hydrochloric acid, saturated sodium bicarbonate solution and brine. Drying, filtration and removal of solvent in vacuo gives 1.25 g (85% yield) of ethyl 4,10-dioxo-1-methyl-1,4,5,10-tetrahydro-1H-[1]-benzazepino[4,3-b]-α-oxo-pyrrole-2-acetate. The sample is purified sufficiently for use in the next reaction step by trituration with ethyl acetate.

Step 6: Preparation of Ethyl 4,10-dioxo-1-methyl-1,4,5,10-tetrahydro-1H-[1]-benzazepino[4,3-b]pyrrole-2-acetate A solution of 0.50 g (0.0015 mole) of ethyl 4,10-dioxo-1-methyl-1,4,5,10-tetrahydro-1H-[1]-benzazepino[4,3-b]-α-oxo-pyrrole-2-acetate in 50 ml anhydrous pyridine containing 0.21 g (0.0030 mole) of imidazole is immersed in an 85° C. oil bath with stirring and a slow stream of hydrogen sulfide gas is bubbled through the reaction for a period of 2 hours. The reaction is then diluted with water, extracted with ethyl acetate and the organic extracts washed successively with 2.5 N hydrochloric acid, saturated sodium bicarbonate solution and brine. Drying, filtration and removal of solvent in vacuo gives after chromatography 0.32 g (59% yield) of ethyl 4,10-dioxo-1-methyl-1,4,5,10-tetrahydro-1H-[1]-benzazepino[4,3-b]pyrrole-2-acetate.

Step 7: Preparation of 4,10-Dioxo-1-methyl-1,4,5,10-tetrahydro-1H-[1]benzazepino[4,3-b]pyrrole-2-acetic acid Sodiuom hydroxide (2.5 N, 25 ml) is added to a solution of 0.25 g of ethyl 4,10-dioxo-1-methyl-1,4,5,10-tetrahydro-1H-[1]benzazepino[4,3-b]pyrrole-2-acetate in 25 ml absolute ethanol. After 2 hours of stirring at room temperature, the reaction mixture is poured into 100 ml of diluted HCl (0.5 N). The resulting white precipitate is filtered, washed with fresh water and air dried to give 0.22 g of off-white solid which is triturated with EtOH to yield 0.19 g (86% yield) of 4,10-dioxo-1-methyl-1,4,5,10-tetrahydro-1H-[1]-benzazepino[4,3-b]pyrrole-2-acetic acid, m.p. 256°–257° C.(d).

Anal. Calc'd for $C_{15}H_{12}N_2O_4$: C, 63.37; H, 4.26; N, 9.86%. Found: C, 63.07; H, 4.36; N, 9.60.

EXAMPLE 7

5,10-Dihydro-1,4-dimethyl-10-oxo-4H-benzo[5,6]cyclohepta[1,2-b]pyrrole-2-acetic acid Step 1: Preparation of Methyl 4-Acetyl-1-methylpyrrol-2-yl-carboxylate To a stirred, dry-ice cooled solution of methyl 1-methylpyrrol-2-yl-carboxylate (1.3 g, 0.0094 m) in 200 cc of 1:1 dried 1,2-dichloroethanenitromethane is added 3.14 g (0.023 m) anhydrous aluminum chloride. After a short time, a solution of acetyl chloride (0.87 g, 0.011 m) in 5 cc of the same solvent mixture is added dropwise to the pyrrole-aluminum chloride system, and the reaction mixture allowed to warm slowly to room temperature. After 2.5 hr, the reaction mixture is cooled in an ice bath and quenched with ice-water. After dilution with methylene chloride, the organic layer is separated, washed two times with fresh water, and the organic solvents removed in vacuo to give 1.54 g (91%) of methyl 4-acetyl-1-methyl-pyrrol-2-yl-carboxylate.

Step 2: Preparation of β-(2-Carbomethoxy)-1-methylpyrrol-4-yl)-β-methylstyrene

To a solution of methyl 4-acetyl-1-methylpyrrole-2-carboxylate (2.72 g, 0.015 m) and benzyltriphenylphosphonium chloride (7.0 g, 0.018 m) in dry dimethylformamide (75 cc) is added, under nitrogen and with stirring, a solution of sodium methoxide (prepared from 0.43 g sodium and 10 cc dried mthanol). After the dropwise addition, the red reaction mixture is allowed to stir at room temperature for a few hours, then heated to a 75° C. (bath temperature) for 36 hours. After cooling, the reaction mixture is diluted with excess dried ether, aged, filtered, the cake washed well with ether, and the combined ether solutions washed three times with ca. equal volumes of water. The dried (anh. sodium sulfate) ether solution is concentrated in vacuo to 6.5 g crude oil, which, after chromatography on silica gel using methylene chloride as eluant, yields 3.14 g (83%) of crystalline β-(2-carbomethoxy-1-methylpyrrol-4-yl)-β-methylstyrene.

Step 3: Preparation of Methyl 1-methyl-4-(α-methyl-β-phenethyl)-pyrrol-2-yl-carboxylate A mixture of β-(2-carbomethoxy-1-methylpyrrol-4-yl)-β-methylstyrene (1.38 g, 0.0054 m), platinum oxide (0.25 g), and glacial acetic acid (20 cc) is reduced under a hydrogen atmosphere (40 psi) until theoretical uptake is obtained.

The reaction mixture is filtered through supercel, the acetic acid removed in vacuo (pump), and the resulting residue purified via HPLC (2% ethyl acetate-hexane/-silica gel) to give 0.84 g (60.4%) of methyl 1-methyl-4-(α-methyl-β-phenethyl)-pyrrol-2-yl-carboxylate.

Step 4: Preparation of Methyl-5-formyl-1-methyl-4-(α-methyl-β-phenethyl)-pyrrol-2-yl-carboxylate A solution of methyl 1-methyl-4-(α-methyl-β-phenethyl)pyrrol-2-yl-carboxylate (0.1 g, 0.39 mmole) in 1,2-dichloroethane (1 cc) is added dropwise to an ice-bath cooled, stirred mixture of dichloroethane (1 cc), N,N-dimethylformamide (0.031 cc), and phosphorous oxychloride (0.04 cc). The resulting mixture is allowed to come to room temperature, then heated in an oil-bath (maximum bath temperature is 105° C.). After two hours of heating, a mixture of dimethylformamide (2 drops) and phosphorous oxychloride (2 drops) is added, followed after an additional one hour of heating by a mixture of 4 drops of each. After heating a total of seven hours, the reaction mixture is allowed to cool and poured into an ice-water mixture (50 cc), extracted with ether, the aqueous layer basified with excess sodium carbonate solution and re-extracted with ether. The combined ether solutions are washed with 10% sodium carbonate solution, dried with anhydrous sodium sulfate and concentrated in vacuo to 0.06 g (54%) of methyl-5-formyl-1-methyl-4-(α-methyl-β-phenethyl)pyrrol-2-yl-carboxylate.

Step 5: Preparation of Methyl 5-carboxy-1-methyl-4-(α-methyl-β-phenethyl)pyrrol-2-yl-carboxylate To a solution of methyl 5-formyl-1-methyl-4-(α-methyl-β-phenethyl)pyrrol-2-yl-carboxylate (0.50 g, 0.00175 m) in acetone (10 cc) while stirring at room temperature, is added dropwise over 8 hours a solution of potassium permanganate (0.55 g, 0.0035 m) in 10 cc of 1:1 acetone-water. After stirring overnight at ambient temperatures, the reaction mixture is diluted with water, treated with sufficient sodium sulfite to reduce excess permanganate, filtered, and the filtrate acidified with dilute hydrochloric acid. The product is filtred, washed well with water and dried under vacuo to afford about 55% yield of methyl 5-carboxy-1-methyl-4-(α-methyl-β-phenethyl)pyrrol-2-yl-carboxylate.

Step 6: Methyl 5,10-dihydro-1,4-dimethyl-10-oxo-4H-benzo[5,6]cyclohepta[1,2-b]pyrrol-2-yl-carboxylate To an ice-bath cooled, stirred solution of methyl 5-carboxy-1-methyl-4-(α-methyl-β-phenethyl)pyrrol-2-yl-carboxylate (0.2 g, 0.66 mmoles) in 2.0 cc dried methylene chloride is added thionyl chloride (0.14 cc, 1.92 mmoles), and the reaction mixture allowed to come to room temperature. The methylene chloride (and one dried benzene flush) is removed in vacuo, and the well-dried residual acid chloride taken up in 2 cc of dried methylene chloride. The ice-cooled solution is then treated with aluminum chloride (0.18 g, 0.0013 m) all at once and the reaction mixture allowed to slowly warm to room temperature overnight. The reaction mixture is then diluted with methylene chloride, quenched with ice-water, the layers separated, the aqueous layer re-extracted with methylene chloride, and the combined organic layers washed well with water and brine. Concentration of the dried (anh. sodium sulfate) organic layer yields 0.15 g (80%) of methyl 5,10-dihydro-1,4-dimethyl-10-oxo-4H-benzo[5,6]cyclohepta-[1,2-b]pyrrol-2-yl-carboxylate as an oil.

Step 7: Preparation of 5,10-Dihydro-1,4-dimethyl-10-oxo-4H-benzo[5,6]cyclohepta[1,2-b]pyrrol-2-yl-carboxylic acid To a suspension of methyl 5,10-dihydro-1,4-dimethyl-10-oxo-4H-benzo[5,6]cyclohepta[1,2-b]pyrrol-2-yl-carboxylate, (0.15 g, 0.53 mmoles) in a stirred, cold mixture of methanol-water (2 cc of a 3:1 mixture) is added 2.5 N sodium hydroxide solution (0.3 cc, 0.75 mmole). A nitrogen atmosphere is maintained throughout the entire period of the reaction. The reaction mixture is allowed to warm to room temperature overnight. Water (ca. 20 cc) is added and, after a short time, the mixture is filtered. Acidification of the filtrate with 2.0 N hydrochloric acid yields 0.13 g (93%) of 5,10-Dihydro-1,4-dimethyl-10-oxo-4H-benzo[5,6]cyclohepta[1,2-b]pyrrol-2-yl-carboxylic acid, m.p. 169°-171° C.

Step 8: Preparation of Methyl 5,10-Dihydro-1,4-dimethyl-10-oxo-4H-benzo[5,6]-cyclohepta[1,2-b]pyrrole-2-acetate To a solution of 5,10-dihydro-1,4-dimethyl-10-oxo-4H-benzo[5,6]cyclohepta[1,2-b]pyrrol-2-yl-carboxylic acid, (0.053 g, 0.196 mmoles) in 4.5 cc dried methylene chloride, stirring, add one small capillary tube droplet of dried N,N-dimethylformamide. The mixture is then ice-cooled, and 9 drops of thionyl chloride added over 20 min. After an additional 20 min, the reaction mixture is allowed to warm to room temperature and stir overnight.

The volatiles (and a 10 cc dry benzene flush) are removed in vacuo, and the residual acid chloride dried on a high-vacuum pump.

The above acid chloride in 3.5 cc dried methylene chloride is added over ca. one minute to a stirred portion of ethereal diazomethane (from 0.5 g N-methyl-N-nitrosourea; the generated diazomethane dissolved in ca. 10 cc ether) with ice-bath cooling. After 15 minutes, the ice-bath is removed, and the mixture allowed to warm to room temperature. Two additional equivalent portions of diazomethane in ether are added at ca. 1 hour intervals, and the mixture allowed to stir overnight. After blowing (nitrogen) off any remaining diazomethane, the mixture is concentrated in vacuo to a glaze that solidifies on standing.

The glaze is dissolved in 4 cc dried methanol, and set in an oil-bath at 87° C. After ca. 5 min, 10 mg of silver oxide is added, followed 30 min later by an additional 10 mg. After a total heating time of 4.5 hrs, the reaction mixture is allowed to cool, filtered, the filter-cake washed well with additional methanol and the combined methanol solutions concentrated in vacuo to a yellow oil. Purification (silica gel GF preparative plates; elution with methylene chloride) yields 27 mg (46%) of methyl 5,10-dihydro-1,4-dimethyl-10-oxo-4H-benzo[5,6]-cyclohepta[1,2-b]pyrrole-2-acetate as an oil.

Step 9: Preparation of 5,10-dihydro-1,4-dimethyl-10-oxo-4H-benzo[5,6]cyclohepta[1,2-b]pyrrol-2-yl-acetic acid To a suspension of methyl 5,10-dihydro-1,4-dimethyl-10-oxo-4H-benzo-[5,6]-cyclohepta[1,2-b]pyrrol-2-acetate (26 mg, 0.087 mmoles) in a mixture of 4 cc ethanol and 0.5 cc water, slight ice-bath cooling, is added 0.06 cc of 2.5 N sodium hydroxide solution. After stirring overnight (nitrogen atmosphere) at ambient temperatures, water (4 cc) is added, the ethanol removed in vacuo, the mixture filtered, and the filtrate acidified with 2 N hydrochloric acid. After aging, the supernatent aqueous solution is decanted from the yellow oil that forms, and the oil washed well with water. The oil is then dissolved in ether, the ether solution dried and concentrated to 20.3 mg (83%) of 5,10-dihydro-1,4-dimethyl-10-oxo-4H-benzo[5,6]cyclohepta[1,2-b]pyrrol-2-yl-acetic acid as a yellow oil.

EXAMPLE 8

Following substantially the same procedure as described in Example 2 but substituting for the m-chlorophenol the appropriately substituted phenols, there are prepared the following compounds of structural formula (IV)

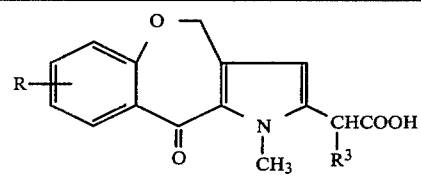

IV

| R | R² | m.p. |
|---|---|---|
| 7-F | H | |
| 7-CH₃ | H | 189–190° |
| 7-OCH₃ | H | 183–185° |
| 7-SCH₃ | H | 180° dec. |

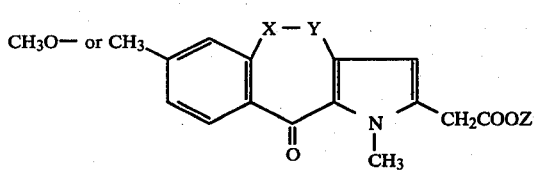

IV

| R | R² | m.p. |
|---|---|---|
| 7-S—CH₃ ↓ O | H | |
| 7-CF₃ | H | |
| 7-SCH₃ | CH₃ | 150–155° dec. |
| 7-SOCH₃ | CH₃ | |
| 7,8-(Cl₂) | H | |
| 7-N(CH₃)₂ \| H | H | |
| 7-NCOCH₃ | H | |
| 7-OCF₃ | H | |
| 7-OH | H | |
| 7-OCH₃, 8-F | H | |
| 7-O\\ CH₂ /  8-O | H | |
| 7-CH₃, 8-F | H | |
| 7,8-diCH₃ | H | |
| 7,8-diCH₃O | H | |
| 7-CH₂CH₃ | H | |
| 7-OCH₂CH₃ | H | |
| 7-CH₂ | H | |
| 7-CN | H | |
| 7-CH₃CO | H | |

EXAMPLE 9

Following substantially the same esterification procedure as described in Example 2, Step 6 (or other conventional esterification procedures well-known in the art) but substituting for the ethanol used therein the appropriate alcohols, there are prepared the following esters useful as analgesic and anti-inflammatory agents of structural formula:

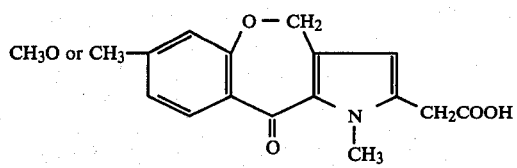

wherein Z is
(a) alkanoyloxyalkyl e.g. 1-(pivaloyloxy)ethyl; 1-(acetoxy)ethyl;
(b) aroyloxyalkyl e.g. 1-(benzoxy)ethyl;
(c) alkoxycarbonyloxyalkyl e.g. 1-(ethoxycarbonyloxy)ethyl
(d) aryloxycarbonyloxyalkyl e.g. 1-(benzyloxycarbonyloxy)ethyl;
(e) trialkylaminoalkyl e.g. choline;
(f) acylaminoalkyl e.g. acetamidoethyl;
(g) imidoalkyl e.g. 1-(succinimido)ethyl;
(h) heterocyclic e.g. phthalidyl, 2-pyridyl;
(i) hydroxyalkyl e.g., hydroxypropyl;
(j) alkoxyalkyl e.g., methoxyethyl, ethoxyethyl, methoxymethyl;
(k) dialkylaminoethyl, e.g. dimethylaminoethyl, dimethylaminopropyl, diethylaminopropyl;
(l) N-pyrrolidinylethyl;
(m) N-piperidinylethyl;
(n) N-morpholinylethyl;
(o) N-ethyl-2-piperidinylethyl;
(p) N-pyrrolidinylmethyl;
(q) N-methyl-2-pyrrolidinylmethyl; or
(r) 4-methyl-1-piperazinylethyl.

EXAMPLE 10

Employing the standard procedures well-known in the art, an acid of structural formula:

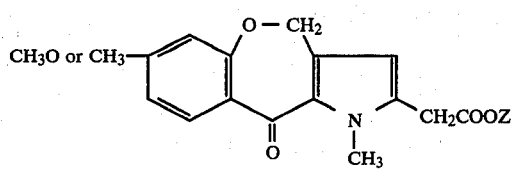

is treated with an appropriate amine to give the following corresponding amides of structural formula:

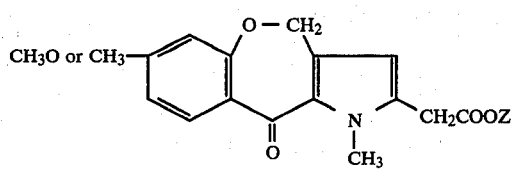

wherein Z' is
(a) alkylamino e.g., ethylamino;
(b) dialkylamino e.g., diethylamino, dimethylamino;
(c) morpholide;
(d) bis(hydroxyethyl)amino;
(e) methylcyclohexylamino; or
(f) glucosamino.

EXAMPLE 11

1,7-Dimethyl-10-oxo-1H-[1]benzoxepino[4,3-b]-pyrrole-2-formaldehyde

Step A: Preparation of 1-(3-methyl-phenoxyacetyl)-2-(N-ethoxycarbonylmethyl-methylamino)-3-t-butoxy-1-propene To a solution of α-t-butoxyacetone (136 g, 1 mol [prepared by Collins oxidation of 1,2-propeneglycol-1-t-butyl ether]) in dry toluene (500 ml) is added sarcosine ethyl ester (120 g, 1 mol) and the resulting mixture is heated to reflux until 18 ml (1 mol) of water has been azeotroped off into a Dean-Stark trap. The resulting mixture is cooled to 0° and pyridine (79 g, 1 mol) is added, followed by addition of m-methyl-phenoxyacetylchloride (198 g, 1 mol) as a solution in toluene (250 ml) over 1 hr. When addition is complete, the reaction is allowed to come to room temperature and stand for 24 hours. The toluene solution is then washed with 1 M H₃PO₄ to remove the pyridine followed by saturated brine, and the organic layer is dried with sodium sulfate (anhydrous). The toluene is then removed in vacuo and the crude product is purified by preparative HPLC to afford pure 1-(3-methylphenoxyacetyl)-2-(N-ethoxycarbonylmethyl-methylamino)-3-t-butoxy-1-propene.

Step B: Preparation of Ethyl 1-methyl-2-t-butoxymethyl)-4-(3-methylphenoxymethyl)pyrrole-5-carboxylate To a solution of 1-(3-methylphenoxyacetyl)-2-(N-ethoxycarbonylmethyl-methylamino)-3-t-butoxy-1-propene (40 g, 0.1 mol) in absolute ethanol (250 ml) is added sodium ethoxide (1.0 g, 0.015 mol) under $N_2$. The reaction is stirred at room temperature and monitored by TLC until all starting material has disappeared. Then acetic acid (0.9 g, 0.015 mole) is added and the mixture taken to dryness in vacuo. The residue is dissolved in ethyl acetate (200 ml) and washed with water (100 ml), then saturated brine (100 ml) and dried over anhydrous sodium sulfate. The solvent is removed and the crude product is purified by preparative HPLC to afford pure ethyl 1-methyl-2-(t-butoxymethyl)-4-(3-methylphenoxymethyl)pyrrole-5-carboxylate.

Step C: Preparation of Ethyl 1-methyl-2-hydroxymethyl)-4-(3-methylphenoxymethyl)pyrrole-5-carboxylate A solution of ethyl 1-methyl-2-(t-butoxymethyl)-4-(3-methylphenoxymethyl)pyrrole-5-carboxylate (3.82 g, 0.01 mol) is allowed to stand in trifluoroacetic acid (50 ml) at room temperature until all starting material is gone by TLC. The TFA is then removed in vacuo and the residue is stirred for 30 minutes with a saturated solution of sodium carbonate in 50% aqueous ethanol (200 ml). Saturated brine (250 ml) is then added, along with ethyl acetate (250 ml) and the layers are separated. The organic layer is washed twice with $H_2O$ (100 ml) then brine (50 ml) and dried over anhydrous sodium sulfate. The solvent is then removed and the residue subjected to preparative HPLC to obtain pure ethyl 1-methyl-2-hydroxymethyl-4-(3-methylphenoxymethyl)pyrrole-5-carboxylate.

Step D: Preparation of Ethyl 1-methyl-2-formyl-4-(3-methylphenoxymethyl)pyrrole-5-carboxylate To a solution of dimethylsulfoxide (390 mg, 5 mmol) in methylene chloride (25 ml) under $N_2$ cooled to $-78°$ C. is added a solution of oxalyl chloride (630 mg, 5 mmol) in methylene chloride (2 ml). The mixture is allowed to stir at $-78°$ for 30 minutes, then a solution of ethyl 1-methyl-2-hydroxymethyl)-4-(3-methylphenoxymethyl)pyrrole-5-carboxylate (1.63 g, 5 mmol) in $CH_2Cl_2$ (5 ml) is added. The resulting solution is stirred for 1 hour, then triethylamine (500 mg, 5 mmol) is added. The reaction is followed by TLC until complete. The resulting solution is washed with water ($2 \times 25$ ml) then saturated brine, and dried over anhydrous sodium sulfate. The crude product is purified by preparative HPLC to afford ethyl 1-methyl-2-formyl-4-(3-methylphenoxymethyl)pyrrole-5-carboxylate.

Step E: Preparation of 1-Methyl-2-formyl-4-(3-methylphenoxymethyl)pyrrole-5-carboxylic acid A sample of ethyl 1-methyl-2-formyl-4-(3-methylphenoxymethyl)pyrrole-5-carboxylate (3.24 g, 10 mmol) is dissolved in hot ethanol (50 ml) and 10% aqueous NaOH is added (10 ml). The resulting mixture is heated at reflux until all starting material has been consumed. The solution is cooled, diluted with water (140 ml) and acidified to pH 2 with 6 N HCl. The resulting two-phase mixture is extracted with ethyl acetate ($2 \times 100$ ml). The combined ethyl acetate layers are then washed with saturated brine (50 ml), and dried over sodium sulfate. The solvent is removed to give a residue which crystallizes on standing. This material is sufficiently pure for use in the next step.

Step F: Preparation of 1,1-dimethyl-10-oxo-1H-[1]-benzoxepino[4,3-b]pyrrole-2-formaldehyde A solution of 1-methyl-2-formyl-4-(3-methylphenoxymethyl)pyrrole-5-carboxylate (1.48, 5 mmol) is dissolved in TFA (20 ml) and TFAA (80 ml) is added. This mixture is stirred at room temperature overnight, then the solvent is removed in vacuo. The residue is purified by HPLC to give 1,1-dimethyl-10-oxo-1H-[1]-benzoxepino[4,3-b]pyrrole-2-formaldehyde and its 9-$CH_3$ isomer.

EXAMPLE 12

Step A: Preparation of Ethyl 2,4-dioxo-5-(3-methylphenoxy)pentanoate

To a solution of α-(m-methylphenoxy)acetone (170 g, 1.0 mol) in dry toluene (500 ml) are added morpholine (87 g, 1.0 mol) and p-tosic acid (1 g). The mixture is refluxed with a Dean-Stark trap until the theoretical amount of water (18 ml) is collected. The mixture is then cooled to room temperature and ethyl oxalyl chloride (136 g, 1.0 mol) in toluene (100 ml) is added, followed by 110 g (1.1 mol) of triethylamine. The mixture is allowed to stand at room temperature for 18 hours, then the toluene solution is washed with 1 N $H_3PO_4$ to remove excess triethylamine and its hydrochloride. The toluene is then removed in vacuo and the resulting residue is stirred with 3 N aqueous HCl (1 l) at room temperature for 1 hr. The aqueous suspension is then extracted with ethyl acetate ($3 \times 500$ ml). The combined ethyl acetate layers are washed with water (500 ml) and saturated brine (250 ml) and dried over anhydrous sodium sulfate. The solvent is then removed to give the product which can then be taken to the next step.

Step B: Preparation of Diethyl 4-(3-methylphenoxy)methyl-pyrrole-2,5-dicarboxylate To a stirred, refluxing mixture of ethyl glycinate hydrochloride (100 g, 0.71 m), ethyl 2,4-dioxo-5-(3-methylphenoxy)pentanoate (187 g, 0.71 m) and benzene (650 ml) under a nitrogen atmosphere is added finely powdered anhydrous potassium carbonate (50 g, 0.36 m) in five portions over one hour, the eliminated water being collected in a Dean-Stark trap until the theoretical amount (12.6 ml) is collected. The mixture is cooled to 5° C., then 750 ml dry ethanol is added and sodium metal (16.5 g, 0.71 mol) is added in small pieces at a rate which permits the internal reaction temperature to be maintained at less than 40° with cooling. Stirring is continued in the ice bath for an additional ½ hour, and the reaction mixture is then poured into a 5-liter separatory funnel containing ether (1 liter) and water (2 liters). The layers are separated and the aqueous layer is re-extracted with ether. The combined ether layers are washed with water and saturated brine. The organic layer is dried over sodium sulfate and concentrated to give a residue which is purified by preparative HPLC to afford diethyl 4-(3-methylphenoxy)methylpyrrole-2,5-dicarboxylate.

Step C: Preparation of Diethyl 1-methyl-4-(3-methylphenoxy)methylpyrrole-2,5-dicarboxylate Diethyl 4-(3-methylphenoxy)methylpyrrole-2,5-dicarboxylate (107 g, 0.41 mol) is dissolved in dry DMF (200 ml) and added dropwise over 10 minutes to an ice-cooled suspension of hexanes-washed sodium hydride (0.41 mol) in dry DMF (400 ml). The resulting mixture was then stirred for one hour, then recooled in an ice bath and treated dropwise over 15 minutes with methyl iodide (30 ml, 0.49 mol). Stirring is continued for an additional thirty minutes, then the mixture is slowly poured into a separatory funnel containing ether (500 ml) and water (one liter). The ether layer was washed with water and saturated brine, then dried over sodium sulfate and the solvent removed in vacuo to give diethyl 1-methyl-4-(3-methylphenoxy)methylpyrrole-2,5-dicarboxylate.

EXAMPLE 13

Step A: Preparation of N-(Ethyloxaloyl)-α-carboethoxy glycine

To a solution of α-carbethoxyglycine hydrochloride (18.3, 0.1 mol) in water (200 ml) is added enough 1 N KOH to bring the pH of the solution to 8.5. Then ethyl oxalyl chloride (20.7 g, 17.0 ml, 0.153 mol) is added dropwise until the pH drops to 7.0, whereupon more 1 N KOH is used to readjust the pH to 8.5. After addition is complete, stirring is continued for 5 minutes, then the solution is cooled to 4° and acidified with 2 N $H_3PO_4$. The solution is then extracted rapidly with cold ethyl acetate (2×150 ml) and the combined organic layers are washed with brine and dried over sodium sulfate. The solvent is then removed to give the product which is carried on directly into the next step.

Step B: Preparation of Diethyl 3-(3-methylphenoxy)methyl pyrrole-2,5-dicarboxylate To a mixture of N-(ethyloxaloyl)-α-carboethoxy glycine (2.47 g, 10 mmol) and m-methylphenylpropargyl ether (1.46 g, 10 mmol) in toluene (15 ml) is added acetic anhydride (1.12 g, 11 mmol) and the mixture is slowly heated and stirred to achieve homogenity. Heating is continued until reflux is attained, and the reflux is maintained for 0.5 hours. The reaction is then cooled and the solvent is removed in vacuo. The residue is taken up is ethylacetate (100 ml) and washed with aqueous sodium bicarbonate, then water and brine, and the organic layer is dried over anhydrous sodium sulfate and the solvent removed to give the crude product. The product is purified by preparative HPLC to afford diethyl 3-(3-methylphenoxy)methyl pyrrole-2,5-dicarboxylate.

EXAMPLE 14

Step A: Preparation of 8-Methyl-1-benzoexpin-4,5-(2H,3H)dione-4-oxine

To a solution of 3,4-dihydro-8-methyl-1-benzoxepin-5(2H)-one (17.6 h, 0.1 mol) in dry ethanol 250 ml are added isoamylnitrite (12.9 g, 0.1 mmol) and sodium ethoxide (13.6 g, 0.2 mol). The mixture is stirred under nitrogen at room temperature until all starting benzoxepinone is consumed by TLC. The reaction is then concentrated to 50 ml and diluted with ether (250 ml) and water (250 ml). The mixture is shaken and the water layer removed, washed again with ether (100 ml), then acidified to pH 4 with 1 N $H_3PO_4$ and extracted with ethyl acetate (2×150 ml). The combined ethylacetate layers are washed with brine (100 ml) and dried over sodium sulfate. The solvent is removed to give crude product which can be used in the next step without further purification.

Step B: Preparation of 8-Methyl-1-benzoxepin-4,5(2H,3H)dione, 4-(O-Acetyl)oxime

A solution of 8-methyl-1-benzoxepin-4,5(2H,3H)dione-4-oxime (4.55 g, 22.2 mmol), acetic anhydride (3.0 ml, 3.3 g, 31 mmol) and ether (40 ml) is refluxed for 2.24 hrs, then poured onto ice, then neutralized with solid sodium bicarbonate. The product is extracted with methylene chloride (100 ml) and the organic layer is washed with saturated brine (50 ml) and dried over sodium sulfate. The solvent is removed to give crude product which solidifies on standing. This material may be used directly in the next step.

Step C: Preparation of Ethyl 4,10-dihydro-1,7-dimethyl-3-ethoxycarbonyl-10-oxo-1H-[1] benzoxepino [4,3-b] pyrrole-2-acetate To a methylene chloride (5.0 ml) solution of trimethyloxonium tetrafluoroborate (1.93 g, 13.0 mmol) is added 8-methyl-1-benzoxepin-4,5(2H,3H)dione-4-(O-acetyl)oxime (2.47 gm, 10 mmol). The mixture is stirred at 25°–30° under nitrogen for 21 hours. The resulting mixture is then added dropwise and with vigorous stirring over 50 minutes to cold, anhydrous triethylamine (17 ml). The resulting mixture is stirred at 0° for 15 min, then the triethylamine is distilled away in vacuo (without heating, and glacial acetic acid (10 ml) and diethyl acetone dicarboxylate (2.2 g, 10 mmol) are added and the resulting mixture is heated to reflux for 15 minutes. The mixture is then cooled, poured into water (100 ml), and the aqueous layer is extracted with ethyl acetate (100 ml) and the organic layer is backwashed with sodium bicarbonate, then washed with saturated brine and dried over sodium sulfate. The solvent is then removed and the product is purified by preparative HPLC to afford ethyl 4,10-dihydro-1,7-dimethyl-3-ethoxycarbonyl-10-oxo-1H-[1]benzoxepino [4,3-b]pyrrole-2-acetate.

The following examples are for the preparation of 1,7-dimethyl- or 1-methyl-7-chloro-4,10-dihydro-10-oxo-1H [1]benzoxepino[4,3-b]pyrrole-2-acetic acid (I).

EXAMPLE 15

A stirred mixture of 1,7-dimethyl-4,10-dihydro-10-oxo-1H[1]benzoxepino[4,3-b]pyrrole-2-acetamide (2.84 g, 0.01 m), ethanol (50 ml) and a solution of sodium hydroxide (4.0 g, 0.1 m) in 20 ml water is heated at 80°–85° C. in an oxygen-free atmosphere for 4 to 6 hours. After the reaction is substantially complete, it is cooled and poured into 250 ml of a stirred ice-water mixture. The resultant mixture is filtered at room temperature, and the filtrate acidified with dilute hydrochloric acid. The precipitate so obtained is filtered, washed well with water and dried to give (I).

The starting amide may also be converted to (I) via acid hydrolysis (e.g., via the procedure of *J. Am. Chem. Soc.*, 63 (1941) 2494 or of *Rec. Trav. Chim* 46 (1927) 600, etc.); via diazotization (e.g., *J. Am. Chem. Soc.* 70 (1948) 3091); *J. Am. Chem. Soc.*, 77, 6011 (1955); or by other routes known of those in the art.

EXAMPLE 16

To a stirred, cooled mixture of 1,7-dimethyl-4,10-dihydro-10-oxo-2-vinyl-1H[1]benzoxepino[4,3-b]pyrrole (A) (7.6 g, 0.03 m) in tetrahydrofuran (100 ml) under nitrogen is added dropwise diborane freshly prepared from adding sodium borohydride (0.38 g) to borontrifluoride etherate (2.3 g). After the reaction is substantially complete the volatiles are removed in vacuo and the resultant crude organoborane is oxidized with dilute chromic oxide solution prepared from mixing chromic acid (26.7 g) and conc. sulfuric acid (23.0 ml) followed by dilution with water to a total volume of 100 ml. The oxidation is substantially complete when a persistent chromic acid color develops. The reaction mixture is treated with aqueous base followed by filtration. The resultant filtrate is acidified with dilute hydrochloric acid to yield (I).

Similar procedure in *J. Am. Chem. Soc.* 68, 2033 (1946), as well as other methods well known in the art, may also be used to convert (A) to (I).

EXAMPLE 17

To a mixture of 2-lithio-2-(trimethylsilyl)-1,3-dithiane (from 1.9 g (0.01 m) 2-trimethylsilyl)dithiane and 6.8 ml of 1.62 m n-butyllithium) in dry tetrahydrofuran at −60° C. (in an oxygen free atmosphere) is added with stirring a tetrahydrofuran solution of 1,7-dimethyl-4,10-dihydro-10-oxo-1[H]benzoxepino[4,3-b]pyrrole-2-carboxaldehyde (2.5 g, 0.01 m). The cooling bath is removed and the mixture is stirred overnight at ambient temperatures followed by warming at about 30°-40° C. until the reaction is substantially complete. The mixture is then added with stirring to an excess of ice-water, and the resultant ketene-thioacetal extracted with methylene chloride. The crude thioacetal obtained from removal of the methylene chloride is then hydrolyzed in the usual manner with mercuric chloride solution to yield (I).

The starting aldehyde may also be converted to (I) by other methods well known to those skilled in the art, e.g., through the use of rhodanine (*J. Am. Chem. Soc.* 62 (1940) 1512, and *Org. Reactions* 1 (1942) 210); through the use of tetraethyldimethylaminomethylene diphosphonate followed by acid hydrolysis (*Agnew. Int. Ed.* 7 391 (1968); through a standard cyanohydrin procedure, (e.g., in *J. Org. Chem.* 21 (1956) 1149); through 1,3-dithiacyclohexylidenetrimethoxyphosphorane with subsequent hydrolysis (*Tet. Letters* (1967) 3201); utilizing tosylmethylisocyanide and subsequent hydrolysis (*Angew. Chem., Intern. Ed. Engl.* 11 (1972) 311); and through a Wittig reaction with methoxymethylenetriphenylphosphorane and subsequent oxidation of the aldehyde formed.

EXAMPLE 18

To a stirred, ice-bath cooled mixture of 1,7-dimethyl-4,10-dihydro-10-oxo-1H[1]benzoxepino[4,3-b]pyrrole-2-ethanol (B) (2.7 g, 0.01 m), tetrahydrofuran (90 ml) and water (10 ml) is added argentic oxide (10 g 0.08 m). After 1 hours, the cooling bath is removed and the resulting mixture stirred at ambient temperatures overnight. Sodium hydroxide solution (5 N, 20 ml) is added, followed after 1 hour by water (200 ml). The mixture is filtered, and the filtrate acidified to give (I).

Oxidation of (B) to (I) may also be accomplished by reagents well known in the art, e.g., air-oxidation catalyzed by platinum, *Tetrahedron* 9 (1960) 67; oxidation with permanganate, *Bull. Chem. Soc. Japan* (1963) 36 1264; with chromic oxide, *J. Am. Chem. Soc.* 78 (1956) 2255 and 82 (1960) 6147, *J. Med. Chem.* 13 (1970) 926; and with nickel peroxides (*J. Org. Chem.* 27 (1962) 1597).

EXAMPLE 19

To a stirred, ice-bath cooled mixture of 1,7-dimethyl-4,10-dihydro-10-oxo-1H[1]benzoxepino-[4,3-b]pyrrole-2-acetaldehyde (2.7 g, 0.01 m) and tetrahydrofuran (50 ml) is added dropwise a solution of m-chloroperbenzoic acid (2.0 g, 0.01 m) in dry tetrahydrofuran at 0° to 10° C. After the reaction is substantially complete, aqueous sodium hydroxide solution (2 N) is added (25 ml) and the reaction mixture is diluted with water (200 ml). It is filtered and the filtrate acidified with 2 N hydrochloric acid to yield crude (I).

Conversion of the starting aldehyde to the corresponding acid (I) may also be accomplished by many other methods well known to those skilled in the art, e.g., utilizing a potassium permanganate-crown ether complex (*J. Am. Chem. Soc.* 94 (1972) 4024); with dithiane chemistry (*J. Org. Chem.* 37 (1972) 2757); with oxygen and a copper-silver oxides catalyst (*Org. Synth. Coll. Vol. IV* 493); with peracids (*Org. Reactions* 9 (1957) 73); with hydrogen peroxide (*Monatah* 86 (1955) 325); with argentic picolinate in dimethylsulfoxide (*Tet. Letters* (1967) 415); with oxides of silver (*Tet. Letters* (1969) 1837), (*Tetrahedron* 24 (1968) 6583), (*J. Am. Chem. Soc.* 90 (1968) 5617); with chromic oxide (*J. Chem. Soc.* C (1970) 1168); with permanganate in acetone or pyridine (*J. Chem. Soc.* C (1970) 1208, *Steroids* 3 (1964) 639.

EXAMPLE 20

To a stirred mixture of 2-acetyl-1,7-dimethyl-4,10-dihydro-10-oxo-1H[1]benzoxepino[4,3-b]pyrrole (C) (6.7 g, 0.025 m) and methylene chloride (200 ml) at 0° C., is added thallium trinitrate on K-10 reagent (44.12 g, 0.029 m) (prepared according to *J. Am. Chem. Soc.* 98 (1976) 6750) and the reaction allowed to warm to room temperature. When the reaction is substantially complete, it is filtered and the filtrate concentrated in vacuo to a residue. The residue is treated with excess sodium hydroxide in aqueous ethanol diluted with water and then acidified with hydrochloric acid to assure efficient precipitation of (I).

The conversion of (C) to (I) may be accomplished by those skilled in the art by other standard procedures, e.g., the standard Willgerodt reaction (*Org. Reactions* 3 2), or other standard combination sequences involving α-oxidation followed by α-keto reduction. The 2-acetyl group may also be converted to the corresponding α-halo compound which undergoes rearrangement by reacting with tert-butyl lithium (*J. Am. Chem. Soc.* (1982) 104 321) to give the desired 2-acetic acid function of (I).

EXAMPLE 21

To a stirred, ice-cooled mixture of 1,7-dimethyl-4,10-dihydro-10-oxo-1H[1]benzoxepino[4,3-b]pyrrole-2-acetyl chloride (3.0 g, 0.01 m) and dioxane (50 ml) is added dropwise a diluted sodium hydroxide solution (0.03 m in 25 ml water). The mixture is allowed to warm to room temperature, diluted to 150 ml with water and filtered. The resultant filtrate is acidified to give (I).

EXAMPLE 22

A stirred mixture of sodium 1,7-dimethyl-4,10-dihydro-10-oxo-1H[1]benzoxepino[4,3-b]pyrrole-2-pyruvate (3.35 g (0.01 m) prepared from 3.13 g of the corresponding acid and 0.4 g NaOH) and a mixture of 1:9 water-dioxane (200 ml) is cooled in ice while 30% aqueous hydrogen peroxide (1.5 g, 0.013 m) is added dropwise over 5 minutes. The mixture is allowed to warm to room temperature and stirred until the reaction is substantially complete. The mixture is diluted with water and treated with 2 N sodium hydroxide solution. It is aged, filtered, and acidified with hydrochloric acid to yield (I).

The starting 2-pyruvate may also be converted to the desired acetic acid of (I) by other oxidation reagents well known in the art.

The corresponding α-ketoaldehyde may be used in place of sodium 1,7-dimethyl-4,10-dihydro-10-oxo-1H[1]benzoxepino [4,3-b]pyrrole-2-pyruvate.

EXAMPLE 23

To a stirred, cooled mixture of α-[1,7-dimethyl-4,10-dihydro-10-oxo-1H[1]benzoxepino[4,3-b]pyrrole-2-]- biacetyl (D) (3.1 g, 0.01 m), dioxane (50 ml) and water (5 ml) is added slowly a solution of periodic acid (2.3 g, 0.01 m) and tetraethyl ammonium hydroxide (0.05 m) in water. When the reaction is substantially complete, it is diluted with an aqueous sodium hydroxide solution (0.2 N, 100 ml), and filtered. The filtrate is acidified with 2 N hydrochloric acid to yield (I).

The above procedure may be used for oxidation of the corresponding acyloin i.e., 1-[1,7-dimethyl-4,10-dihydro-10-oxo-1H[1]-benzoxepino[4,3-b]-pyrrole-2-yl]-3-hydroxybutanone-2 (D') to give (I). However, potassium hydrogencarbonate or a similar base may be used instead of the tetraethylammonium hydroxide mentioned above. (D') may also be converted to (I) by the following procedure:

A mixture of (D') (3.13 g, 0.01 m), pyridine (80 ml) and cuprous chloride (1.98 g, 0.01 m) is stirred at room temperature while oxygen is bubbled through the solution until the reaction is substantially complete. The mixture is then diluted with aqueous sodium hydroxide solution (20 ml of 2 N sodium hydroxide in 150 ml water). It is aged, filtered, and the resulting filtrate acidified with hydrochloric acid to give (I).

The above procedure may also be used for the 2-pyruvate (D), and for the reverse acyloin, i.e., 4-[1,7]dimethyl-4,10-dihydro-10-oxo-1H-[1]benzoxepino-[4,3-b]pyrrol-2-yl]-3-hydroxybutan-2-one.

Many other procedures well known in the art may be used to convert the 2-pyruvate (D) and the acyloins to (I) including periodate-permanganate, *Can. J. Chem.* 33 1701 (1955) or 34 (1413 (1956); *J. Org. Chem.* 24 741 (1959) and others.

EXAMPLE 24

1-[1,7-Dimethyl-4,10-dihydro-10-oxo-1H[1]benzoxepino-[4,3-b]-pyrrol-2-yl]butan-2,3-diol (E)

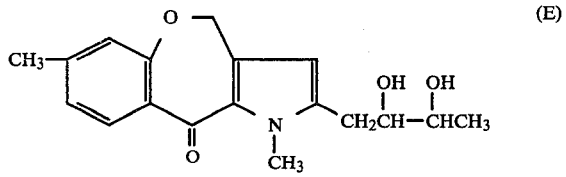

and its two possible aminoalcohol analogs may each be oxidized to (I) according to the procedure of Example 39 or Example 24. (E) may also be oxidized to (I) directly with silver and silver oxide in aqueous ethanolic potassium with water (150 ml) containing 2 N sodium hydroxide solution (20 ml), aged, filtered, and the filtrate acidified with hydrochloric acid to give I.

The above procedure may also be used for the diketone (A), and for the reverse acyloin, i.e., 4-[1,7-dimethyl-4,10-dihydro-10-oxo-1H-[1]benzoxepino-[4,3-b]pyrrol-2-yl]-3-hydroxybutanone-2.

Many other procedures well known to one skilled in the art may be used to convert the diketone and acyloins above, to I, including periodate-permanganate (*Can. J. Chem.* 33 1701 (1955); 34 1413 (1956); *J. Org. Chem.* 24 741 (1959)) others.

Using the above procedures with the symmetrical glycol yields two molecules of I per molecule starting compound.

EXAMPLE 25

To a stirred mixture of 2-allyl-1,7-dimethyl-4,10-dihydro-10-oxo-1H[1]benzoxepino[4,3-b]pyrrole (1.34 g, 0.005 m) and t-butanol (250 ml) with cooling is added dropwise a mixture of sodium metaperiodate (6.4 g, 0.03 m) and potassium permanganate (20 mg) in water (minimum for solution). The mixture is kept at pH 8 by continuous addition of 5% aqueous potassium carbonate solution, and stirred until the color of the permanganate is discharged. The mixture is diluted with excess dilute base, filtered, and acidified with 2 N hydrochloric acid to yield (I).

Conversion of (F) to I may be accomplished by other methods well known to those skilled in the art, e.g., by the method in Ber. 75B (1942) 656, using ozone; with ruthenium tetroxide and sodium metaperiodate (*J. Am. Chem. Soc.* 85 (1963) 3419); or by a phase transfer oxidation with permanganate (*J. Org. Chem.* 42 (1977) 3749).

EXAMPLE 26

A stirred mixture of 1,7-dimethyl-4,10-dihydro-10-oxo-2-($\beta,\beta,\beta$-trifluoroethyl)-1H[1]benzoxepino[4,3-b]pyrrole (3.1 g, 0.01 m), ethanol (50 ml), and a solution of potassium hydroxide (5.6 g, 0.1 m) in 20 ml water is heated at 80°–85° C. in an inert atmosphere until no starting material is indicated by TLC. The mixture is allowed to cool, added to 250 ml of a stirred ice-water mixture, filtered, and the filtrate acidified with dilute hydrochloric acid to yield (I).

The corresponding 2-($\beta,\beta,\beta$-trichloro- or tribromoethyl) analog may be used in place of the starting trifluoroethyl compound to give (I).

EXAMPLE 27

To a stirred, cold mixture of [1,7-dimethyl]-4,10-dihydro-10-oxo-1H[1]benzoxepino[4,3-b]pyrrole-2-yl-methoxymethyl ketone (3.0 g, 0.01 m) and methanol is added sodium borohydride (0.114 g, 0.003 m) over ca. 15 minutes. The reaction mixture is allowed to warm slowly to room temperature over several hours. Excess dilute hydrochloric acid and methylene chloride are added, the layers separated, and the methylene chloride layer concentrated in vacuo to the corresponding crude alcohol which is dehydrated with pyridine-phosphorus oxychloride to yield the intermediate, an enol-ether. This is taken up in ether and treated with perchloric acid (Ber. 95 (1962) 2514) to yield 1,7-dimethyl-4,10-dihydro-10-oxo-1H[1]benzoxepino[4,3-b]pyrrole-2-acetaldehyde, which is oxidized according to Example 24 to give I.

EXAMPLE 28

To a stirred, ice-bath cooled mixture of triethyl 1,7-dimethyl-4,10-dihydro-10-oxo-1H[1]benzoxepino[4,3-b]pyrrole-2-orthoacetate (G) (3.9 g, 0.01 m), ethanol (50 ml) and dioxane (50 ml) is added 10% hydrochloric acid (20 ml) over 30 minutes. The reaction mixture is then stirred at ambient temperatures until the reaction is substantially complete. Ethanol (50 ml) is added, followed by an aqueous solution of sodium hydroxide (10 g in 20 ml water) over one hour. The resulting mixture is stirred at ambient temperatures no starting material is indicated by TLC analysis. The mixture is diluted with water (250 ml), aged, filtered, and acidified with hydrochloric acid to yield (I).

EXAMPLE 29

A mixture of 1,7-dimethyl-4,10-dihydro-10-oxo-1H[1]benzoxepino[4,3-b]pyrrole-2-acetamidine hydrochloride (2.8 g, 0.01 m), ethanol (50 ml) and a solution of potassium hydroxide (5.6 g, 0.10 m) in 20 ml water is heated at ca. 80° C. in an oxygen-free atmosphere for 4 to 6 hours. It is cooled, added to 250 ml of a stirred ice-water mixture, and warmed to room temperature. The resultant mixture is filtered, and the filtrate acidified with hydrochloric acid (2 N) to yield (I).

Alternatively, acid hydrolysis may be used to convert the acetamidine to (I). Step-wise hydrolysis via the amide may also be employed.

The corresponding cyclic amidine-analog, i.e., 1-[1,7-dimethyl-4,10-dihydro-10-oxo-1H[1]benzoxepino[4,3-b]pyrrole-2-ylmethyl]-imidazoline is also converted to (I) by the basic hydrolysis outlined above.

EXAMPLE 30

To a stirred, ice-cooled mixture of the anhydride (H) of 1,7-dimethyl-4,10-dihydro-10-oxo-1H[1]benzoxepino[4,3-b]-pyrrole-2-acetic acid (0.01 m) and dioxane (50 ml) is added a solution of sodium hydroxide (1.2 g, 0.02 m) in water (20 ml) over 30 minutes. The mixture is allowed to warm to room temperature and stirred until thin-layer chromatography indicates the absence of (H). After dilution with water (80 ml), the mixture is acidified with 2 N hydrochloric acid, aged, and filtered to afford (I). Similarly, asymmetric anhydride, for example, the anhydride formed between 1,7-dimethyl-4,10-dihydro-10-oxo-1H[1]benzoxepino[4,3-b]-pyrrole-2-acetic acid and its 1-benzyl analog may also be converted to (I).

EXAMPLE 31

Methyl 2-[1,7-dimethyl-4,10-dihydro-10-oxo-1H[1]benzoxepino[4,3-b]pyrrole-2-yl]-2-hydroxy acetate (3.15 g, 0.01 m) is heated gently in excess thionyl chloride or other chlorinating agent (or at lower temperatures with pyridine present) until the reaction is substantially complete. The excess thionyl chloride is removed in vacuo, the residue washed and with benzene (2×10 ml) followed by removal of the solvent and any remaining thionylchloride in vacuo. The residual α-chloro ester is then taken up in tetrahydrofuran (50 ml), cooled, and treated with sodium borohydride (0.003 m) at ca. 15° C. until reduction is complete. Water (5.0 ml) is added, followed by 2 N sodium hydroxide solution (20 ml), and the resulting mixture stirred overnight at ambient temperatures. After dilution with excess water followed by filtration, the filtrate is acidified with 2.0 N hydrochloric acid to yield (I).

Alternatively, the α-hydroxy or α-halo compound may be reduced directly to (I) via standard catalytic and chemical reduction procedures well-known in the art.

EXAMPLE 32

Methyl[1,7-dimethyl-4,10-dihydro-10-oxo-1H[1]benzoxepino[4,3-b]pyrrole-2-yl-]-2-aminoacetate (J) (prepared from the corresponding acid with diazomethane) (3.14 g, 0.01 m) is converted to its N-mesyl derivative via treatment with mesyl chloride in pyridine. The crude mesylate is then stirred and heated in 20% aqueous sodium hydroxide (50 ml)-ethanol (25 ml), to gentle reflux under a nitrogen atmosphere. Hydroxylamine-O-sulfonic acid (25 g) is added portionwise and the resultant mixture is kept at the same temperature for an additional hour. The reaction mixture is cooled and then diluted with water. It is filtered and the filtrate acidified with 2 N hydrochloric acid to yield (I).

The conversion of (J) to (I) may also be accomplished via initial conversion of the amino group to an alcohol or halide followed by reduction (see Example 36); or by oxidative decarboxylation to the corresponding aldehyde followed by subsequent chain extension as described in Example 22.

EXAMPLE 33

A mixture of methyl 3-(1,7-dimethyl-4,10-dihydro-10-oxo-1H[1]benzoxepino[4,3-b]pyrrole-2-yl)-3-keto propionate (6.54 g, 0.02 m; prepared from the corresponding acid and diazomethane) and p-toluenesulfonhydrazine (3.8 g, 0.02 m) is heated in methanol (200 ml) until the hydrazone formation is substantially complete. After methanol is removed, the residue is taken up in dry chloroform (20 ml), and cooled to −10° C. Catecholborane (2.5 g, 0.021 m) is then added and the mixture is stirred at −10° C. for one hour followed by addition of sodium acetate trihydrate (8.2 g, 0.06 m). The resultant mixture is stirred and allowed to come to room temperature overnight. The reaction mixture is treated with water and the chloroform layer separated and concentrated to yield methyl 3-(1,7-dimethyl-4,10-dihydro-10-oxo-1H[1]benzoxepino[4,3-b]pyrrole-2-)-propionate. Shortening of the propionate side chain of this material is accomplished in a variety of ways. For example, the following procedure utilizing the classic Barbier-Wieland method:

To an ice-bath cooled, stirred mixture of the purified propionic methyl ester obtained above (4.0 g, 0.013 m) and ether (50 ml) is added phenylmagnesium bromide (from bromobenzene (4.32 g, 0.0275 m) and magnesium turnings (0.7 g, 0.029 g atoms)) in ether (50 ml) over ca. fifteen minutes. The resulting mixture is to stirred at ambient temperatures for one hour, and treated with 6 N hydrochloric acid. The resulting carbinol is isolated and heated in excess acetic anhydride to give the diphenylethylene derivative. Oxidation as in Example 30 gives (I).

It should be noted that the Barbier-Wieland procedure as described above may be repeated twice in order to obtain (I) from methyl 4-(1,7-dimethyl-4,10-dihydro-10-oxo-1H[1]benzoxepino[4,3-b]pyrrole-2-)-butyrate.

Other chain shortening procedures may also be used for example, (1) conversion of the side-chain propionic and butyric esters to their α-hydroxy and α-amino analogs followed by oxidative cleavage as shown in Example 39 and 40;

(2) microbial and enzymatic degradations of the side-chain acids; and (3) shortening of the side-chain by the Varrentrapp modification (*Biochem. J.* 50 163 (1951)) of the Barbier-Wieland reaction, as well as the silver salt degradation modification of the Hunsdieker reaction.

EXAMPLE 34

To a stirred, cooled mixture of 3-[1,7-dimethyl-4,10-dihydro-10-oxo-1H[1]benzoxepino[4,3-b]pyrrole-2-yl]-2-hydroxypropionic acid (3.15 g, 0.01 m), benzene (50 ml) and acetic acid (10 ml) is added portionwise lead-tetraacetate (5.0 g, 0.011 m) while maintaining the temperature below 15° C. The mixture is stirred for an additional hour and is filtered. The filtrate is concentrated in vacuo and the residue dissolved in tetrahydrofuran (50 ml) and cooled. m-Chloroperbenzoic acid (2.0 g, 0.01 m) in a small volume of tetrahydrofuran is added dropwise and the reaction mixture allowed to warm to room temperature. After the reaction is substantially complete, it is treated with 2 N sodium hydroxide (25 ml) and diluted with water (200 ml). The resulting mixture is filtered and the filtrate acidified with 2 N hydrochloric acid to yield crude (I).

The corresponding hydroxyaldehyde, i.e. 3-[1,7-dimethyl-4,10-dihydro-10-oxo-1H[1]benzoxepino[4,3-b]pyrrole-2-yl]-2-hydroxypropionaldehyde, and its acetals, may be converted to (I) similarly.

EXAMPLE 35

To a stirred, ice-bath cooled mixture of 3-[1,7-dimethyl-4,10-dihydro-10-oxo-1H[1]benzoxepino[4,3-b]pyrrole-2-]alanine (K) (3.14 g, 0.01 m), tetrahydrofuran (50 ml) and aqueous sodium hydroxide (0.5 g, 0.0125 m in 10 ml water) is added argentic oxide (10 g, 0.08 m) prepared by the method of Jirsa, *Z. Anorg. Allgem. Chem.* 225 (1935) 302). The reaction mixture is allowed to warm to room temperature and stirred until the reaction is essentially complete. Excess aqueous sodium hydroxide is added and the resulting mixture filtered. The filtrate is then acidified with dilute hydrochloric acid to give (I).

EXAMPLE 36

To a stirred solution of potassium hydroxide (4.5 g, 0.08 m) in water (4 ml) at 75° C. and under a nitrogen atmosphere is added methyl 4-[1,7-dimethyl-4,10-dihydro-10-oxo-1H[1]benzoxepino[4,3-b]pyrrole-2-yl]-3-ketobutyrate (L) (3.4 g, 0.01 m) in portions. After stirring for an additional five hours at 75° C., the reaction mixture is cooled, diluted with water and aged. It is washed with ether and then acidified with 2 N hydrochloric acid to give (I).

Conversion of (L) to (I) may also be accomplished by other procedures well known in the art, for example, the oxidative-cleavage of the corresponding enol by lead tetraacetate, permanganate or similar reagents; or by an enzymatic procedure.

EXAMPLE 37

The conversion of 1,7-dimethyl-4,10-dihydro-10-oxo-1H[1]benzoxepino[4,3-b]pyrrole-2-yl-methanol to (I) is accomplished by a variety of methods, including the stepwise conversion to the corresponding 2-halomethyl compound, the corresponding acetonitrile, followed by hydrolysis (see Example 48); formation of the grignard reagent of the 2-halomethyl compound followed by treatment with carbon dioxide (see Example 43); direct carbonation with carbon monoxide in presence of a rhodium catalyst (*Chem. Comm.* (1968) 1578); and oxidation to the corresponding aldehyde followed by elongative-oxidation (see Example 22).

EXAMPLE 38

To a stirred mixture of sodium cyanide (7.1 g), water (150 ml) and acetonitrile (150 ml) at 20° C. and under nitrogen is added a solution of 2-(chloromethyl)-1,7-dimethyl-4,10-dihydro-10-oxo-1H[1]benzoxepino[4,3-b]pyrrole (M) (4.0 g, 0.0145 m) in acetonitrile (75 ml) over 0.5 hour. After an additional 3-4 hours, the mixture is added slowly to ice-water (800 ml) with stirring and the resulting precipitate collected by filtration. Subsequently the precipitated cyano compound is hydrolyzed with aqueous ethanolic sodium hydroxide to afford (I) as described in Example 48.

Alternatively, the 2-chloromethyl compound may be converted to (I) by reacting it with magnesium and treating the resulting grignard reagent with carbon dioxide (*Can. J. Chem.* 42 (1964) 1488), or by other methods well known to those skilled in the art.

The corresponding bromomethyl, tosyl- and mesyl compounds may be used in place of (M).

EXAMPLE 39

A stirred mixture of 1,7-dimethyl-4,10-dihydro-10-oxo-1H[1]benzoxepino[4,3-b]pyrrole (N) (5.7 g, 0.025 m), bronze powder (0.1 g) and an inert diluent (e.g., decane), under a nitrogen atmosphere is heated to 135° C. Ethyldiazoacetate (2.3 g, 0.02 m) is then added slowly. After the reaction is substantially complete, the reaction mixture is cooled and diluted with methylene chloride. It is stirred for about 10 minutes before it is filtered and concentrated in vacuo to a residue. Chromatography on silica gel using methylene chloride as eluant yields the ethyl ester of (I) which in turn is hydrolyzed in the usual manner to afford (I).

Alternatively, (N) is converted to (I) via reaction with ethyl oxalylchloride under Friedel-Crafts conditions followed by reduction of the resulting α-keto group and subsequent hydrolysis, of the ethyl ester.

Furthermore, treatment of (N) with maleic acid in the presence of boron trifluoride followed by decarboxylation yields 1,7-dimethyl-4,10-dihydro-10-oxo-1H[1]benzoxepino[4,3-b]pyrrole-2-(α-methyl) acetic acid. (*Ann.* 486 (1931) 211).

Finally, direct alkylation with haloacetic acids such as chloroacetic acid in the presence of suitable catalysts such as KBr or KBr/Fe$_2$O$_3$ yields the acetic acid directly (*J. Am. Chem. Soc.* 72 (1950) 4302; *Syn.* (1970) 628).

EXAMPLE 40

To a stirred, cooled (0° C.) solution of diisopropylamine (12.5 g, 0.124 m) in dry tetrahydrofuran (40 ml) under a nitrogen atmosphere is added N-butyllithium (0.124 m) and the solution stirred for 10 minutes followed by cooling to −78° C. A mixture of 7-chloro-1,2-dimethyl-4,10-dihydro-10-oxo-1H[1]benzoxepino[4,3-b]pyrrole (31.3 g, 0.12 m), dimethylcarbonate (11.7 g, 0.13 m) and tetrahydrofuran (50 ml) is then added dropwise over 10 min. The bath is then removed and the mixture allowed to warm to room temperature and is stirred for four hours. Water (50 ml) is added and the reaction mixture is further stirred overnight. Aqueous sodium hydroxide is then added and the mixture is filtered. The filtrate is acidified to yield 7-chloro-4,10-dihydro-1-methyl-10-oxo-1H[1]benzoxepino[4,3-b]pyrrole-2-acetic acid.

EXAMPLE 41

To a stirred mixture of 1,7-dimethyl-4,10-dihydro-10-oxo-2-propargyl-1H[1]benzoxepino[4,3-b]-pyrrole (O) (2.65 g, 0.01 m), dioxane (300 ml) and water (25 ml) at 0°–5° C. is added dropwise an aqueous solution of potassium permanganate (3.2 g, 0.02 m). The mixture is stirred at ambient temperatures until the reaction is complete. After excess permanganate is destroyed by bisulfite, the mixture is basified with 2 N sodium hydroxide, diluted with water, filtered, and the filtrate acidified with 2 N hydrochloric acid to yield (I).

Conversion of (O) to (I) may also be accomplished by other methods known in the art, e.g., cleavage-oxidation by ozone, of *Carbohydrate Res.* (1966) 2 315; and oxidation by peroxytrifluoroacetic acid, *J. Am. Chem. Soc.* 86 (1964) 4866.

EXAMPLE 42

A stirred portion of 1,7-dimethyl-4,10-dihydro-10-oxo-1H[1]benzoxepino[4,3-b]pyrrole-2-malonic acid (P) is slowly heated in an oil-bath under an inert atmosphere until the generation of carbon dioxide commences. It is held at this temperature until carbon dioxide evolution ceases. The residue is cooled and purified by crystallization from isopropanol-water to give (I).

Other well-known methods to decarboxylate (P) include heating in a dilute aqueous acid/cosolvent mixture; percolating through an ion-exchange (acidic) column with a suitable solvent; heating in an inert solvent or a suitable inert solid.

EXAMPLE 43

A stirred mixture of 1,7-dimethyl-4,10-dihydro-10-oxo-1H[1]benzoxepino[4,3-b]pyrrole-2-acetonitrile (2.7 g, 0.01 m) ethanol (50 ml) and aqueous sodium hydroxide (4.0 g, 0.1 m in 20 ml water) is heated at 80°–85° C. in an inert atmosphere for 4 to 6 hours. It is cooled, and poured into 250 ml of a stirred ice-water mixture. The resulting mixture is filtered at room temperature, and the filtrate acidified with dilute hydrochloric acid to yield (I).

The starting 2-acetonitrile may also be converted to the corresponding acid by well-known methods, e.g., acid hydrolysis; conversion to an iminoether followed by hydrolysis, conversion to an aldehyde followed by mild oxidation; and conversion to an ortho ester followed by hydrolysis under mild conditions.

EXAMPLE 44

A stirred mixture of ethyl 1,7-dimethyl-4,10-dihydro-10-oxo-1H[1]benzoxepino[4,3-b]pyrrole-2-acetimidate (3.13 g, 0.01 m), ethanol (50 ml), and aqueous sodium hydroxide (4.0 g, 1.0 m in 20 ml water) is heated at 80°–85° C. in an inert atmosphere for 5 hours. The reaction mixture is cooled and poured into 250 ml of stirred ice-water mixture. It is filtered at room temperature and the filtrate acidified with 2 N hydrochloric acid to yield (I).

The 2-acetimidate may also be hydrolyzed in acidic media to the corresponding ethyl ester, which in turn is hydrolyzed under mild, basic conditions to yield (I).

EXAMPLE 45

Mercuric oxide (4.3 g, 0.02 m) is added in small portions to a gently refluxing mixture of ethyl 1,7-dimethyl-4,10-dihydro-10-oxo-1H[1]benzoxepino[4,3-b]pyrrole-2-thiolacetate (3.3 g, 0.02), mercuric chloride and aqueous 70% acetone (50 ml). The resulting mixture is kept an hour at this temperature. After cooling, excess dilute sodium hydroxide solution is added and the mixture is stirred and then filtered. The filtrate is acidified with 2 N hydrochloric acid to yield I.

EXAMPLE 46

A cold solution of sodium hypobromite is prepared from 1.6 g. of sodium hydroxide, 3.2 g of bromine, and 10 g of ice and water. To this solution is added with stirring 1-[7-chloro-4,10-dihydro-1-methyl-10-oxo-1H[1]benzoxepino[4,3-b]pyrrole-2-yl]propan-2-one (Q) (1.5 g, 0.005 m), while keeping the temperature below 10° C. The resulting mixture is stirred at low temperature for an additional 4 hours before water and ether are added. The layers are separated and the aqueous layer is treated with a sufficient amount of sodium bisulfite. The treated aqueous layer is filtered and the filtrate acidified with 2 N hydrochloric acid to give crude 7-chloro-4,10-dihydro-1-methyl-10-oxo-1H[1]benzoxepino[4,3-b]pyrrol-2-acetic acid.

(Q) may also be converted to 7-chloro-4,10-dihydro-1-methyl-10-oxo-1H[1]benzoxepino[4,3-b]pyrrol-2-acetic acid by other procedures well known in the art, e.g., by selective α-oxidation of the 2-propanone sidechain to the α-ketoaldehyde followed by oxidation.

EXAMPLE 47

To a stirred mixture of t-butyl 1,7-dimethyl-4,10-dihydro-10-oxo-1H[1]benzoxepino[4,3-b]pyrrole-2-acetate (R) (3.3 g) in dry benzene (50 ml) is added a few small crystals of anhydrous p-toluenesulfonic acid. The resultant mixture is refluxed under $N_2$ until the evolution of isobutylene ceases. It is cooled and diluted with petroleum ether or hexane (75 ml). After aging, the mixture is filtered to yield (I).

In place of p-toluenesulfonic acid, methanesulfonic or other suitable acid may be used.

The t-butyl ester may also be removed by stirring (R) in trifluoroacetic acid (with or without an inert solvent as diluent) at ambient temperatures.

EXAMPLE 48

A stirred mixture of ethyl 2-[1,7-dimethyl-4,10-dihydro-10-oxo-1H[1]benzoxepino[4,3-b]pyrrol-2-yl]-cyanoacetate (3.4 g, 0.01 m), ethanol (50 ml) and aqueous potassium hydroxide (5.6 g, 1.0 m in 20 ml water) is heated in an inert atmosphere for six hours at 85° C. It is cooled, diluted with water and filtered. The filtrate is acidified with hydrochloric acid to give a precipitate which is collected and washed well with water. It is dried and heated slowly with stirring under a nitrogen atmosphere until carbon dioxide generation commences. The material is then heated at this temperature until carbon dioxide evolution ceases. Crystallization of the crude product from i-propanol-water yields pure (I).

Alternatively, an inert diluent or solvent, and/or a copper catalyst may be used during the decarboxylation.

EXAMPLE 49

A stirred, cooled solution of 2-[1,7-dimethyl-4,10-dihydro-10-oxo-1H[1]benzoxepino[4,3-b]pyrrol-2-methylene-]-4,4,6-trimethyl-5,6-dihydro-1,3-4H-oxazine (S) (3.2 g) in dioxane (100 ml) is treated with 10% hydrochloric acid (20 ml) over ca. 20 min and the resultant mixture stirred at ambient temperatures until the reaction is complete. Dilution of the reaction mixture with water followed by filtration yields I.

EXAMPLE 50

A mixture of benzyl 1,7-dimethyl-4,10-dihydro-10-oxo-1H[1]benzoxepino[4,3-b]pyrrole-2-acetate (3.75 g, 0.01 m), ethyl acetate (50 ml), anhydrous magnesium oxide (2.0 g), and 10% palladium on carbon (0.2 g) is stirred in a hydrogen atmosphere (1 atmos.) at 20° C. until the theoretical amount of hydrogen (0.01 m) is absorbed. The mixture is filtered, the volatiles removed in vacuo (5) and the residue recrystallized from i-propanol-water to yield (I).

Alternatively, the benzyl ester may be hydrolyzed in an aqueous alcoholic base such as potassium hydroxide/ethanol followed by acidification.

EXAMPLE 51

To a stirred, cold (10°–15° C.) mixture of boron trifluoride-methanol complex (20 ml) containing silver carbonate (1.7 g, 0.006 m) is added 2-(bromoacetyl)-1,7-dimethyl-4,10-dihydro-10-oxo-1H[1]benzoxepino[4,3-b]pyrrole (T) (3.5 g, 0.01 m), and the reaction is stirred until no starting material is left. Volatiles are removed in vacuo, and the residue is hydrolyzed in aqueous methanolic potassium hydroxide. The resulting mixture is diluted with water, filtered, and the filtrate acidified with dilute hydrochloric acid to yield (I).

(T) may also be converted to I by other wellknown methods, e.g., by reduction of the 2-bromo group to the 2-acetyl group, followed by conversion to I as in Example 25.

EXAMPLE 52

To a stirred mixture of 1,7-dimethyl-4,10-dihydro-2-ethynyl-10-oxo-1H[1]benzoxepino[4,3-b]-pyrrole (6.2 g, 0.025 m) in dry tetrahydrofuran (60 ml) at −15° C. is added 9.6 ml of 1.96 M borane in the same solvent. During the addition, the temperature is maintained at 0±5° C. After completion of the borane addition, the mixture is stirred for an additional hour at 3±2° C. followed by addition of methanol (2 ml) and cooling in a dry-ice/acetone bath. Maintaining the reaction temperature at about −20° C. to 0° C. a solution of m-chloroperbenzoic acid (16.7 g, 0.083 m) in tetrahydrofuran (about 10 ml) is added dropwise. After stirring at room temperature for one hour, the reaction mixture is basified with 3 N sodium hydroxide solution, diluted with water and filtered. The filtrate is acidified with dilute hydrochloric acid to precipitate the crude product which upon crystallization affords pure (I).

Conversion of the starting ethynl compound may also be accomplished by other methods well known in the art, e.g., by the procedure of McDonald and Schwab, *J. Am. Chem. Soc.* 86 (1964) 4866, or by the procedure in *Annales de Chimie* 16 (1931) 309.

It has been found that the compounds of Formula I possess anti-inflammatory, antipyretic and analgesic activities. Particularly they are effective in the prevention and inhibition of edema and granuloma tissue formation as shown by the phlogistically induced rat foot edema assay.

More specifically the compounds of the present invention are useful for reducing inflammation and relieving pain in a variety of diseases, e.g., rheumatoid arthritis, osteoarthritis, gout, infectious arthritis and rheumatic fever. At similar dosage levels, they are as effective as zomepirac-type compounds known in the art but exhibit a lower incidence of side effects.

The rat foot edema assay for determining anti-inflammatory activity is based on the ability of the compounds of Formula I to inhibit the edema induced by the injection of an inflammatory (phlogistic) agent into the tissues of the foot of a rat. Several groups of six male rats (Sprague Dawley strain, 150±30 g each) are given orally the compounds to be tested one hour before 0.1 ml of a 1% suspension of carragenin in 0.5% methocel is injected into the planar surface of each rat's right hind paws. Immediately and again three hours later, the foot volume is measured and recorded. The difference between the initial and final volumes is a measurement of the edema produced. Usually the compounds to be tested are suspended or dissolved in 0.5% methocel, and their activities measured against that produced by a known anti-inflammatory agent e.g., zomepirac (U.S. Pat. No. 3,952,012) according to standard procedure. The activity of a tested compound is also compared with that produced by a "control" rat which receives only the methocel solution. A test of 3 mg/kg, 10 mg/kg plus one dose of 30 mg/kg are usually given.

The results of these tests are as follows:

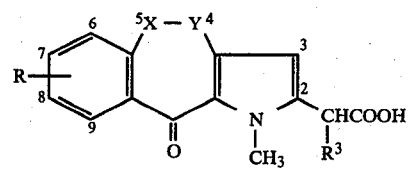

| R | X—Y | $R^3$ | Dose (mg/kg) | Edema (C.F.E) % inhibition |
|---|---|---|---|---|
| 7-Cl | —CH$_2$CH$_2$— | H | 3 | 29.9 |
|  |  |  | 10 | 41.5 |
|  |  |  | 30 | 57.5 |
| 7-Cl | —CH$_2$CH$_2$— | CH$_3$ | 20 | 36.8 |
|  |  |  | 30 | 59.0 |
| 7-Cl | —O—CH$_2$— | H | 3 | 46.0 |
|  |  |  | 10 | 64.0 |
|  |  |  | 30 | 54.0 |
| 7-Cl | —O—CH$_2$— | CH$_3$ | 30 | 60.0 |
| 7-Cl | —S—CH$_2$— | H | 30 | 51.0 |
| 7-Cl | —CH$_2$—O— | H | 20 | 50.0 |
| 7-OCH$_3$ | —O—CH$_2$ | H | 3 | 44.0 |
|  |  |  | 30 | 61.0 |
| 7-CH$_3$ | —OCH$_2$— | H | 3 | 32.1 |
|  |  |  | 10 | 39.9 |
|  |  |  | 20 | 42.6 |
| 7-F | —O—CH$_2$— | H | 10 | 31.0 |
|  |  |  | 30 | 40.0 |

This invention also relates to a method of treating inflammation comprising the adminitration of a compound of Formula I as the active constituent.

The active compounds of Formula I and the pharmaceutical compositions thereof are found to be superior than Zomepirac and related analgesic/antiinflammatory agents in the Gastric Hemorrhage Lesion Formation Assay (GHLF). In other words, they induce less gastric irritation than Zompirac. The GHLF test is conducted according to the following procedure:

Rats (Sprague-Dawley, Males, 120–180 gm) are fasted overnight and dosed orally with drug suspended in 0.5% methylcellulose. The drug concentration is adjusted so that each animal received 1.0 ml/100 gm body weight. Four hours later the animals are killed by asphixiation in carbon dioxide, the stomachs removed, cut open and everted. The mucosal lining is washed and examined under 3X magnification. The lesions are identified as perforations of the gastric mucosa, many of which perforate right through the wall of the stomach.

The results are expressed in two ways, the average number of lesions per stomach, and the number of animals in the group showing at least one lesion.

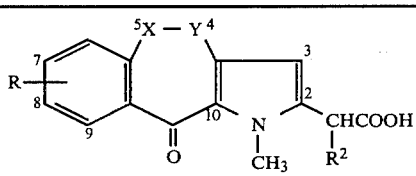

| R | —X—Y | Dosage level mg/kg | No. of animals per group | Ave. lesions per animal | Animals with lesions |
|---|---|---|---|---|---|
| 7-Cl | —CH₂—CH₂— | 100 | 5 | 0.2 | 1/5 |
|  |  | 300 | 5 | 0 | 0/5 |
|  |  | 600 | 5 | 1.8 | 4/5 |
| 7-Cl | —O—CH₂ | 90 | 6 | 5.0 | 5/6 |
|  |  | 60 | 6 | 0 | 0/6 |
| 7-OCH₃ | —OCH₂ | 90 | 6 | 1.0 | 2/6 |
|  |  | 120 | 6 | 4.0 | 4/6 |
| 7-SCH₃ | —O—CH₂ | 10 | 6 | 0 | 0/6 |
|  |  | 90 | 6 | 13.5 | 5/6 |
| 7-CH₃ | —O—CH₂ | 30 | 6 | 0 | 0/6 |
|  |  | 60 | 6 | 0.16 | 1/6 |
|  |  | 90 | 6 | 0.33 | 2/6 |
|  |  | 120 | 6 | 3.3 | 4/6 |

For treatment of inflammation, the compounds of this invention may be administered orally, parenterally, topically or rectally to a patient in need of such treatment in dosage unit formulations containing a non-toxic pharmaceutically acceptable carrier, preferably in tablet or capsule form. The term parenteral as used above includes subcutaneous, intravenous, intramuscular or intrasternal injection or infusion techniques.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharamaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for the manufacture of tablets. These excipients may be for example, inert diluents such as calcium carbonate sodium carbonate, lactose, calcium phosphate or sodium phosphate; granulating and disintergrating agents, for example, maize starch, or alginic acid; binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example peanut oil., liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing of wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example thyl, or n-propyl, p-hydroxy benzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such a those set forth above, and flavoring agents may be added to provide a palatable oral preparation. These compositions may be preserved by the addition of an antioxidant such as ascorbic acid.

Dispersible powders and granules suitable for preparation of an aqueous suspensin by the addition of water provide the active ingredient in admixture with a dispersing or wetting agent, suspending agent and one or more preservatives. Suitable dispersing or wetting and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucorse. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions, or suspensions, etc., containing the anti-inflammatory agents are employed.

Dosage levels of the order to 0.2 mg to 140 mg per kilogram of body weight per day are useful in the treatment of the above-indicated conditions (10 mg to 7 gms per patient per day). For example, inflammation is effectively treated and anti-pyretic and analgesic activity manifested by the administration from about 0.5 to 50 mg of the compound per kilogram of body weight per day (25 mg to 3.5 gms per patient per day). Advantageously, from about 2 mg to about 20 mg per kilogram of body weight per daily dosage produces highly effective results (100 mg to 4 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

What is claimed is:

1. A compound having the formula:

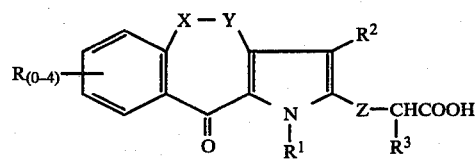

(I)

or a pharmaceutically acceptable alkali metal, alkaline metal or quaternary ammonium salt thereof wherein there are 0-4 R groups and R is
  (a) hydrogen;
  (b) lower alkyl;
  (c) halo-loweralkyl;
  (d) hydroxy or lower alkoxy;
  (e) halo;
  (f) lower alkylthio;
  (g) lower alkylsulfinyl;
  (h) lower alkylsulfonyl;
  (i) lower alkenyl;
  (j) phenyl;
  (k) substituted phenyl wherein the substituent is loweralkyl, loweralkylsulfonyl, loweralkylsulfinyl, loweralkylthio, loweralkoxy, chloro or fluoro;
  (l) carboxy;
  (m) carbalkoxy;
  (n) cyano;
  (o) loweralkylamino or amino;
  (p) di(loweralkyl)amino;
  (q) lower alkanoyl; or
  (r) benzoyl or substituted benzoyl wherein the substituent is fluoro, chloro, loweralkyl or loweralkoxy;

$R^1$ is
  (a) hydrogen;
  (b) lower alkyl;
  (c) lower alkenyl;
  (d) lower alkanoyl;
  (e) phenyl or substituted phenyl;
  (f) benzoyl or substituted benzoyl;
  (g) benzyl or substituted benzyl;
  (h) lower alkoxy;
  (i) lower alkylamino;
  (j) di(loweralkyl)amino; or
  (k) hydroxy $C_{1-6}$alkyl;

Z is
  (a) $-(CH_2)_{0-n}$, n being 0-10;
  (b) $-CO(CH_2)_{1-n}-$;
  (c) $-(CH_2)_{1-n}-CO-$; or

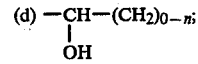

$R^2$ is
  (a) hydrogen;
  (b) lower alkyl;
  (c) lower alkenyl;
  (d) lower alkoxy; or
  (e) $-CH_2OH$;
  (f) halo; or
  (g) phenyl or substituted phenyl;

$R^3$ is hydrogen, lower alkyl, hydroxy, loweralkoxy, or halo; and

X-Y is

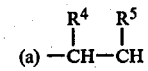

wherein $R^4$ and $R^5$ independently are hydrogen, loweralkyl loweralkoxy or halo;
  (b) $-CR^4=CR^5-$;
  (c) $-O-CH_2-$;
  (d) $-CH_2-O-$;
  (e) $-S-CH_2-$;
  (f) $-CH_2-S-$;
  (g) $-CO-O-$;
  (h) $-O-CO-$;
  (i) $-CO-NH-$; or
  (j) $-NH-CO-$.

2. The compound of claim 1 wherein:
R is
   (a) hydrogen;
   (b) $C_{1-4}$ alkyl;
   (c) halo-$C_{1-3}$alkyl;
   (d) $C_{1-3}$alkoxy;
   (e) chloro or fluoro;
   (f) $C_{1-3}$alkylthio;
   (g) $C_{1-3}$alkylsulfinyl;
$R^1$ is hydrogen, or $C_{1-6}$ lower alkyl;
Z is
   (a) —$CH_2)_{0-5}$—;
   (b) —$(CH_2)_{1-5}$—CO—; or (c) —CH—$(CH_2)_{1-5}$—;
        |
        OH $R^2$ is
   (a) hydrogen;
   (b) $C_{1-3}$ alkyl;
   (c) $C_{1-3}$ alkoxy;
$R^3$ is hydrogen, $C_{1-4}$ alkyl, $C_{1-4}$ alkoxy, chloro or fluoro; and
X-Y is
   (a) —O—$CH_2$—O—; or
   (b) —O—$CH_2$—;
   (c) —$CH_2$—S—; or
   (d) —S—$CH_2$.
3. The compound of claim 1 wherein:
R is
   (a) methyl or ethyl;
   (b) $C_{1-3}$ haloalkyl;
   (c) methoxy or ethoxy;
   (d) chloro or fluoro;
   (e) methylthio;
   (f) methylsulfinyl; or
   (g) 7,8-methylenedioxy;
$R^1$ is hydrogen, methyl, ethyl or propyl;
Z is as previously defined;
$R^2$ is
   (a) hydrogen; or
   (b) $C_{1-3}$ alkyl;
$R^3$ is hydrogen, methyl methoxy or fluoro; and
X-Y is
   (a) —O—$CH_2$—; or
   (b) —S—$CH_2$—.
4. The compound of claim 1 which is
   (a) 4,10-dihydro-1,7-dimethyl-10-oxo-1H[1]benzoxepino[4,3-b]pyrrole-2-acetic acid; or
   (b) 7-methoxy-4,10-dihydro-1-methyl-10-oxo-1H[1]benzoxepino[4,3-b]pyrrole-2-acetic acid.
5. A pharmaceutical composition for treating inflammatory conditions, fever and pain in mammalian species comprising a non-toxic pharmaceutical carrier and an effective amount of a compound of formula:

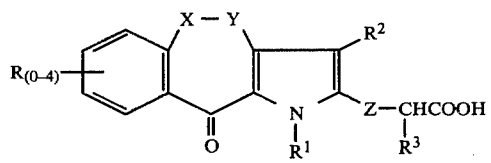

(I)

or a pharmaceutically acceptable alkali metal, alkaline metal or quaternary ammonium salt thereof wherein there are 0-4 R groups and R is (a) hydrogen;
   (b) lower alkyl;
   (c) halo-loweralkyl;
   (d) hydroxy or lower alkoxy;
   (e) halo;
   (f) lower alkylthio;
   (g) lower alkylsulfinyl;
   (h) lower alkylsulfonyl;
   (i) lower alkenyl;
   (j) phenyl;
   (k) substituted phenyl wherein the substituent is loweralkyl, loweralkylsulfonyl, loweralkylsulfinyl, loweralkylthio, loweralkoxy, chloro or fluoro;
   (l) carboxy;
   (m) carbalkoxy;
   (n) cyano;
   (o) loweralkylamino or amino;
   (p) di(loweralkyl)amine;
   (q) lower alkanoyl; or
   (r) benzoyl or substituted benzoyl wherein the substituent is fluoro, chloro, loweralkyl or loweralkoxy;
$R^1$ is
   (a) hydrogen;
   (b) lower alkyl;
   (c) lower alkenyl;
   (d) lower alkanoyl;
   (e) phenyl or substituted phenyl;
   (f) benzoyl or substituted benzoyl;
   (g) benzyl or substituted benzyl;
   (h) lower alkoxy;
   (i) lower alkylamino;
   (j) di(loweralkyl)amino; or
   (k) hydroxy $C_{1-6}$alkyl;
Z is
   (a)—$(CH_2)_{0-n}$, n being 0–10;
   (b) —$CO(CH_2)_{1-n}$—;
   (c) —$(CH_2)_{1-n}$—CO—; or (d) —CH—$(CH_2)_{0-n}$;
        |
        OH $R^2$ is
   (a) hydrogen;
   (b) lower alkyl;
   (c) lower alkenyl;
   (d) lower alkoxy; or
   (e) —$CH_2OH$;
   (f) halo; or
   (g) phenyl or substituted phenyl;
$R^3$ is hydrogen, lower alkyl, hydroxy, loweralkoxy, or halo; and
X-Y is $R^4$ $R^5$
         |    |
   (a) —CH—CH wherein $R^4$ and $R^5$ independently are hydrogen, loweralkyl loweralkoxy or halo;
   (b) —$CR^4$=$CR^5$—;
   (c) —O—$CH_2$—;
   (d) —$CH_2$—O—;
   (e) —S—$CH_2$—;
   (f) —$CH_2$—S—;
   (g) —CO—O—;

(h) —O—CO—;
(i) —CO—NH—; or
(j) —NH—CO—.

6. The pharmaceutical composition of claim 5 wherein
R is:
  (a) hydrogen;
  (b) $C_{1-4}$ alkyl;
  (c) halo-$C_{1-3}$alkyl;
  (d) $C_{1-3}$alkoxy;
  (e) chloro or fluoro;
  (f) $C_{1-3}$alklythio;
  (g) $C_{1-3}$alkylsulfinyl;
$R^1$ is hydrogen or $C_{1-6}$ lower alkyl;
Z is
  (a) —(CH$_2$)$_{0-5}$—;
  (b) —CO(CH$_2$)$_{1-5}$—;
  (c) —(CH$_2$)$_{1-5}$—CO—; or (d) $-\underset{\underset{\text{OH}}{|}}{\text{CH}}-(\text{CH}_2)_{0-5}-$;

$R^2$ is
  (a) hydrogen;
  (b) $C_{1-3}$ alkyl;
  (c) $C_{1-3}$ alkoxy;
$R^3$ is hydrogen, $C_{1-4}$ alkyl, $C_{1-4}$ alkoxy, chloror or fluoro; and
X-Y is
  (a) —CH$_2$—O—;
  (b) —O—CH$_2$—;
  (c) —CH$_2$—S—; or
  (d) —S—CH$_2$.

7. The pharmaceutical composition of claim 5 wherein:
R is
  (a) methyl or ethyl;
  (b) $C^{1-3}$ haloalkyl;
  (c) methoxy or ethoxy;
  (d) chloro or fluoro;
  (e) methylthio;
  (f) methylsulfinyl; or
  (g) 7,8-methylenedioxy;
$R^1$ is hydrogen, methyl, ethyl or propyl;
Z is as previously defined;
$R^2$ is
  (a) hydrogen or
  (b) $C_{1-3}$ alkyl;
$R^3$ is hydrogen, methyl, methoxy or fluoro; and
X-Y is
  (a) —O—CH$_2$—; or
  (b) —S—CH$_2$—.

8. The pharmaceutical composition of claim 5 wherein the compound is
  (a) 4,10-dihydro-1,7-dimethyl-10-oxo-1H[1]benzoxepino[4,3-b]pyrrole-2-acetic acid; or
  (b) 7-methoxy-4,10-dihydro-1-methyl-10-oxo-1H[1]benzoxepino[4,3-b]pyrrole-2-acetic acid.

9. A method of treatment of inflammatory conditions, fever and pain which comprises the administration to a mammalian species in need of such treatment an effective amount of a compound of formula:

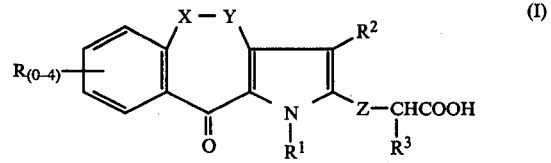

or a pharmaceutically acceptable alkali metal, alkaline metal or quaternary ammonium salt thereof wherein there are 0–4 R groups and R is
  (a) hydrogen;
  (b) lower alkyl;
  (c) halo-loweralkyl;
  (d) hydroxy or lower alkoxy;
  (e) halo;
  (f) lower alkylthio;
  (g) lower alkylsulfinyl;
  (h) lower alkylsulfonyl;
  (i) lower alkenyl;
  (j) phenyl;
  (k) substituted phenyl wherein the substituent is loweralkyl, loweralkylsulfonyl, loweralkylsulfinyl, loweralkylthio, loweralkoxy, chloro or fluoro;
  (l) carboxy;
  (m) carbalkoxy;
  (n) cyano;
  (o) loweralkylamino or amine;
  (p) di(loweralkyl)amino;
  (q) lower alkanoyl; or
  (r) benzoyl or substituted benzoyl wherein the substituent is fluoro, chloro, loweralkyl or loweralkoxy;
$R^1$ is
  (a) hydrogen;
  (b) lower alkyl;
  (c) lower alkenyl;
  (d) lower alkanoyl;
  (e) phenyl or substituted phenyl;
  (f) benzoyl or substituted benzoyl;
  (g) benzyl or substituted benzyl;
  (h) lower alkoxy;
  (i) lower alkylamino;
  (j) di(loweralkyl)amino; or
  (k) hydroxy $C_{1-6}$alkyl;
Z is
  (a) —(CH$_2$)$_{0-n}$, n is being 0–10;
  (b) —CO(CH$_2$)$_{1-n}$—;
  (c) —(CH$_2$)$_{1-n}$—CO—; or (d) 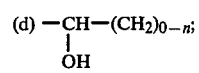

$R^2$ is
  (a) hydrogen;
  (b) lower alkyl;
  (c) lower alkenyl;
  (d) lower alkoxy; or
  (e) —CH$_2$OH;
  (f) halo; or
  (g) phenyl or substituted phenyl;
$R^3$ is hydrogen, lower alkyl, hydroxy, loweralkoxy, or halo; and
X-Y is (a) 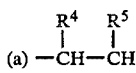

wherein $R^4$ and $R^5$ independently are hydrogen, loweralkyl loweralkoxy or halo;
- (b) $-CR^4=CR^5-$;
- (c) $-O-CH_2-$;
- (d) $-CH_2-O-$;
- (e) $-S-CH_2-$;
- (f) $-CH_2-S-$;
- (g) $-CO-O-$;
- (h) $-O-CO-$;
- (i) $-CO-NH-$; or
- (j) $-NH-CO-$.

10. The method of claim 9 wherein:
there are 0–4 R groups and R is
- (a) hydrogen;
- (b) $C_{1-4}$ alkyl;
- (c) halo-$C_{1-3}$alkyl;
- (d) $C_{1-3}$alkoxy;
- (e) chloro or fluoro;
- (f) $C_{1-3}$-alkylthio;
- (g) $C_{1-3}$alkylsulfinyl;

$R^1$ is hydrogen or $C_{1-6}$ lower alkyl;
Z is
- (a) $-(CH_2)_{0-5}-$;
- (b) $-CO(CH_2)_{1-5}-$;
- (c) $-(CH_2)_{1-5}-CO-$; or (d) 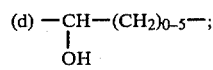

$R^2$ is
- (a) hydrogen;
- (b) $C_{1-3}$ alkyl;
- (c) $C_{1-3}$ alkoxy;

$R^3$ is hydrogen, $C_{1-4}$ alkyl, $C_{1-4}$ alkoxy, chloro or fluoro; and
X-Y is
- (a) $-CH_2-O-$;
- (b) $-O-CH_2-$;
- (c) $-CH_2-S-$; or
- (d) $-S-CH_2$.

11. The method of claim 9 wherein:
there are 0–4 R groups and R is
- (a) methyl or ethyl;
- (b) $C_{1-3}$ haloalkyl;
- (c) methoxy or ethoxy;
- (d) chloro or fluoro;
- (e) methylthio;
- (f) methylsulfinyl; or
- (g) 7,8-methylenedioxy;

$R^1$ is hydrogen, methyl, ethyl or propyl;
Z is as previously defined;
$R^2$ is
- (a) hydrogen; or
- (b) $C_{1-3}$ alkyl;

$R^3$ is hydrogen, methyl, methoxy or fluoro; and
X-Y is
- (a) $-O-CH_2-$; or
- (b) $-S-CH_2-$.

12. The method of claim 9 wherein the compound is
(a) 4,10-dihydro-1,7-dimethyl-10-oxo-1H[]benzoxepino[4,3-b]pyrrole-2-acetic acid; or (b) 7-methoxy-4,10-dihydro-1-methyl-10-oxo-1H[1]benzoxepino[4,3-b]pyrrole-2-acetic acid.

13. A process for preparing a compound of structural formula:

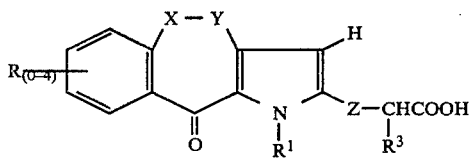

wherein R, $R^1$, Z, $R^3$ an X-Y are as previously defined in claim 1 comprising treating a precursor diacid of the structural formula:

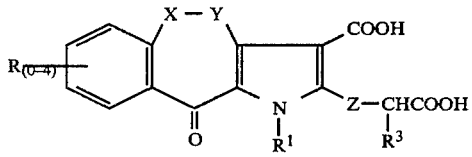

or the corresponding t-butyl or benzhydryl ester thereof with an acid.

14. A process for preparing a compound of formula

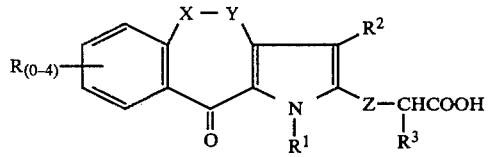

(I)

or a pharmaceutically acceptable alkali metal, alkaline metal or quaternary ammonium salt thereof wherein there are 0–4 R groups and R is
- (a) hydrogen;
- (b) lower alkyl;
- (c) halo-loweralkyl;
- (d) hydroxy or lower alkoxy;
- (e) halo;
- (f) lower alkylthio;
- (g) lower alkylsulfinyl;
- (h) lower alkylsulfonyl;
- (i) lower alkenyl;
- (j) phenyl;
- (k) substituted phenyl wherein the substituent is loweralkyl, loweralkylsulfonyl, loweralkylsulfinyl, loweralkylthio, loweralkoxy, chloro or fluoro;
- (l) carboxy;
- (m) carbalkoxy;
- (n) cyano;
- (o) loweralkylamino or amino;
- (p) di(loweralkyl)amino;
- (q) lower alkanoyl; or
- (r) benzoyl or substituted benzoyl wherein the substituent is fluoro, chloro, loweralkyl or loweralkoxy;

$R^1$ is
- (a) hydrogen;
- (b) lower alkyl;
- (c) lower alkenyl;
- (d) lower alkanoyl;
- (e) phenyl or substituted phenyl;

(f) benzoyl or substituted benzoyl;
(g) benzyl or substituted benzyl;
(h) lower alkoxy;
(i) lower alkylamino;
(j) di(loweralkyl)amino; or
(k) hydroxy $C_{1-6}$alkyl;

Z is
(a) —$(CH_2)_{0-n}$, n being 0–10;
(b) —$CO(CH_2)_{1-n}$—;
(c) —$(CH_2)_{1-n}$—CO—; or (d) 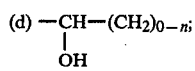

$R^2$ is
(a) hydrogen;
(b) lower alkyl;
(c) lower alkenyl;
(d) lower alkoxy; or
(e) —$CH_2OH$;
(f) halo; or
(g) phenyl or substituted phenyl;

$R^3$ is hydrogen, lower alkyl, hydroxy, loweralkoxy, or halo; and

X-Y is (a) 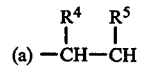

wherein $R^4$ and $R^5$ independently are hydrogen, loweralkyl loweralkoxy or halo;
(b) —$CR^4$=$CR^5$—;
(c) —O—$CH_2$—;
(d) —$CH_2$—O—;
(e) —S—$CH_2$—;
(f) —$CH_2$—S—;
(g) —CO—O—;
(h) —O—CO—;
(i) —CO—NH—; or
(j) —NH—CO—;

comprising treating a precursor ester of the structural formula:

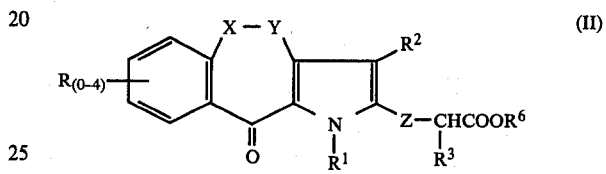

(II)

wherein
R, $R^1$, $R^2$, $R^3$ and —X—Y— are as previously defined; and
$R^6$ is lower alkyl; or an acid-removable protecting group selected from a group consisting of t-butyl, benzhydryl, benzyl, trityl, trichloroethyl, β-trimethylsilylethyl and trimethylsilyl; with water and an acid or a base.

* * * * *